(12) United States Patent
Gupta et al.

(10) Patent No.: US 6,306,939 B1
(45) Date of Patent: Oct. 23, 2001

(54) POLY-TRISARYL-1,3,5-TRIAZINE CARBAMATE ULTRAVIOLET LIGHT ABSORBERS

(75) Inventors: Ram Baboo Gupta, Stamford; Dennis John Jakiela, Orange, both of CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/335,787

(22) Filed: Jun. 18, 1999

Related U.S. Application Data

(60) Provisional application No. 60/090,249, filed on Jun. 22, 1998.

(51) Int. Cl.$^7$ ........................ C08K 5/3492; C07D 251/14
(52) U.S. Cl. .......................... 524/100; 544/215; 544/216; 252/403
(58) Field of Search ............................. 524/100; 544/215, 544/216; 252/403

(56) References Cited

U.S. PATENT DOCUMENTS

| | | | |
|---|---|---|---|
| 3,043,709 | 7/1962 | Amborski | 117/7 |
| 3,118,837 | 1/1964 | Briggs | 210/232 |
| 3,242,175 | 3/1966 | Duennenberger et al. | 260/248 |
| 3,244,708 | 4/1966 | Duennenberger et al. | 260/248 |
| 3,249,608 | 5/1966 | Biland et al. | 260/248 |
| 3,268,474 | 8/1966 | Hardy et al. | 260/45.8 |
| 3,309,220 | 3/1967 | Osteen | 117/33.3 |
| 3,423,360 | 1/1969 | Huber et al. | 260/47 |
| 3,487,505 | 1/1970 | Chisholm et al. | 18/13 |
| 3,557,265 | 1/1971 | Chisholm et al. | 264/47 |
| 3,843,371 | 10/1974 | Piller et al. | 96/84 |
| 4,314,933 | 2/1982 | Berner | 260/45.75 |
| 4,325,863 | 4/1982 | Hinsken et al. | 624/111 |
| 4,331,586 | 5/1982 | Hardy | 525/186 |
| 4,338,244 | 7/1982 | Hinsken et al. | 524/109 |
| 4,344,876 | 8/1982 | Berner | 524/91 |
| 4,353,965 | 10/1982 | Olson et al. | 428/412 |
| 4,426,471 | 1/1984 | Berner | 524/91 |
| 4,426,472 | 1/1984 | Berner | 524/99 |
| 4,481,664 | 11/1984 | Linger et al. | 382/8 |
| 4,518,686 | 5/1985 | Sasaki et al. | 430/512 |
| 4,540,623 | 9/1985 | Im et al. | 428/220 |
| 4,619,956 | 10/1986 | Susi | 524/87 |
| 4,668,588 | 5/1987 | Kishima | 428/412 |
| 4,740,542 | 4/1988 | Susi | 524/87 |
| 4,775,707 | 10/1988 | Slongo et al. | 524/91 |
| 4,826,978 | 5/1989 | Migdal et al. | 544/216 |
| 4,853,471 | 8/1989 | Rody et al. | 548/261 |
| 4,937,026 | 6/1990 | Goossens et al. | 264/129 |
| 4,948,666 | 8/1990 | Paul et al. | 428/334 |
| 4,960,863 | 10/1990 | Rosenquist | 528/480 |
| 4,962,142 | 10/1990 | Migdal et al. | 524/100 |
| 4,973,702 | 11/1990 | Rody et al. | 548/261 |
| 4,992,322 | 2/1991 | Curry et al. | 428/215 |
| 5,004,770 | 4/1991 | Cortolano et al. | 524/99 |
| 5,006,577 | 4/1991 | Behrens et al. | 524/95 |
| 5,030,731 | 7/1991 | Slongo et al. | 548/260 |
| 5,064,883 | 11/1991 | Behrens et al. | 524/95 |
| 5,071,981 | 12/1991 | Son et al. | 544/198 |
| 5,084,570 | 1/1992 | Burdeska et al. | 544/216 |
| 5,106,891 | 4/1992 | Valet | 524/91 |
| 5,112,890 | 5/1992 | Behrens et al. | 524/95 |
| 5,124,378 | 6/1992 | Behrens et al. | 524/95 |
| 5,175,312 | 12/1992 | Dubs et al. | 549/307 |
| 5,185,445 | 2/1993 | Meuwly et al. | 544/216 |

(List continued on next page.)

FOREIGN PATENT DOCUMENTS

| | | |
|---|---|---|
| 2032669 | 6/1991 | (CA) . |
| 2162645 | 5/1996 | (CA) . |
| 480 091 | 12/1969 | (CH) . |
| 484 695 | 3/1970 | (CH) . |
| 39 22 496 | 1/1991 | (DE) . |
| 43 16 611 | 11/1993 | (DE) . |
| 43 16 622 | 11/1993 | (DE) . |
| 43 16 876 | 11/1993 | (DE) . |
| 309 400 | 3/1989 | (EP) . |
| 309 401 | 3/1989 | (EP) . |
| 309 402 | 3/1989 | (EP) . |
| 434 608 | 6/1991 | (EP) . |
| 434 619 | 6/1991 | (EP) . |
| 444 323 | 9/1991 | (EP) . |
| 520 938 | 12/1992 | (EP) . |
| 531 258 | 3/1993 | (EP) . |
| 589 839 | 3/1994 | (EP) . |
| 591 102 | 4/1994 | (EP) . |
| 649 841 | 4/1995 | (EP) . |
| 654 469 | 5/1995 | (EP) . |
| 704 437 | 4/1996 | (EP) . |
| 706 083 | 4/1996 | (EP) . |
| 1 033 387 | 6/1966 | (GB) . |
| 2 269 819 | 2/1994 | (GB) . |
| 2 290 745 | 1/1996 | (GB) . |
| 2 293 823 | 4/1996 | (GB) . |
| WO 94/04515 | 3/1994 | (WO) . |
| WO 95/22959 | 8/1995 | (WO) . |
| WO 96/28431 | 9/1996 | (WO) . |

OTHER PUBLICATIONS

Ullmann's Encyclopedia of Industrial Chemistry; 5$^{th}$ Ed.; vol. A18; pp. 368, 426, 429–471, 491, 500.

B.L. Diffey and J. Robson; "A new substrate to measure sunscreen protection factors throughout the ultraviolet spectrum," *J. Soc. Cosmet. Chem.*, May/Jun. 1989, 127–133.

*Primary Examiner*—Kriellion A. Sanders
(74) *Attorney, Agent, or Firm*—Tyler A. Stevenson

(57) ABSTRACT

The present invention relates to novel carbamate containing trisaryl-1,3,5-triazines and the use thereof as an ultraviolet light absorber. In particular, the presently claimed compounds comprise a carbamate triazine polymer which is particularly useful, either alone or in combination with other additives, including other ultraviolet light absorbers and stabilizers, in stabilizing a polymeric film or molded article from degradation due to exposure to actinic radiation.

53 Claims, No Drawings

U.S. PATENT DOCUMENTS

| | | | |
|---|---|---|---|
| 5,189,084 | 2/1993 | Birbaum et al. | 524/100 |
| 5,198,498 | 3/1993 | Valet et al. | 525/125 |
| 5,204,473 | 4/1993 | Winter et al. | 546/188 |
| 5,216,052 | 6/1993 | Nesvadba et al. | 524/108 |
| 5,252,643 | 10/1993 | Nesvadba | 524/111 |
| 5,288,788 | 2/1994 | Shieh et al. | 524/495 |
| 5,298,067 | 3/1994 | Valet et al. | 106/506 |
| 5,300,414 | 4/1994 | Leppard et al. | 430/507 |
| 5,322,868 | 6/1994 | Valet et al. | 524/89 |
| 5,323,868 | 6/1994 | Kawashima | 180/65.4 |
| 5,354,794 | 10/1994 | Stevenson et al. | 524/100 |
| 5,369,140 | 11/1994 | Valet et al. | 522/75 |
| 5,412,008 | 5/1995 | Michaelis | 524/100 |
| 5,420,204 | 5/1995 | Valet et al. | 525/125 |
| 5,445,872 | 8/1995 | Suhadolnik et al. | 428/215 |
| 5,459,222 | 10/1995 | Rodgers et al. | 528/73 |
| 5,461,151 | 10/1995 | Waterman | 544/216 |
| 5,478,935 | 12/1995 | Reinehr et al. | 544/180 |
| 5,556,973 * | 9/1996 | Stevenson et al. | 544/216 |
| 5,637,706 * | 6/1997 | Stevenson et al. | 544/216 |

* cited by examiner

POLY-TRISARYL-1,3,5-TRIAZINE CARBAMATE ULTRAVIOLET LIGHT ABSORBERS

This Application claims benefit of Provisional No. 60/090,249 filed Jun. 22, 1998.

BACKGROUND OF THE INVENTION

1. Field of the Invention

This invention relates generally to novel poly-trisaryl-1,3,5-triazine carbamates and the use thereof to protect against actinic radiation.

2. Description of Related Art

Exposure to sunlight and other sources of ultraviolet radiation are known to cause degradation of a variety of materials, especially polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are trisaryl-1,3,5-triazines, in which at least one of the aryl rings has a hydroxyl group ortho to the point of attachment to the triazine ring. In general this class of materials is well known in the art. Disclosures of a number of such trisaryl-1,3,5-triazines can be found in the following publications, all of which are incorporated by reference herein for all purposes as if fully set forth: U.S. Pat. Nos. 3,118,887, 3,242,175, 3,244,708, 3,249,608, 3,268,474, 3,843,371, 4,619,956, 4,740,542, 4,775,707 4,826,978, 4,962,142, 5,030,731, 5,071,981, 5,084,570, 5,106,891, 5,185,445, 5,189,084, 5,198,498, 5,288,778, 5,298,067, 5,322,868, 5,354,794, 5,369,140, 5,412,008, 5,420,204, 5,461,151 and 5,478,935; Canadian Patent Documents CA A1-2162645 and CA 2,032,669; UK Patent Documents GB1033387 and GB-A-2293823; Swiss Patent Documents CH480091 and CH484695; European Patent Documents EP-A-0434608, EP-A-0434619, EP-A-0444323, EP-A-0649841, EP-A-0654469, EP-A-0704437, EP-A-0706083; and PCT Patent Documents WO95/22959 and WO96/28431.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para- to the point of attachment to the triazine ring. This second substituent can be "non-reactive," as in the case of an alkyloxy group, or "reactive" as in the case of a hydroxyalkyloxy (active hydrogen reactive site) or (meth)acryloyl (ethylenic unsaturation reactive site) group. The former are typically referred to as "non-bondable" trisaryl-1,3,5-triazines, and the latter are referred to as "bondable" trisaryl-1,3,5-triazines.

Many polymer additives (such as ultraviolet light stabilizers) may suffer from a disadvantage that they volatilize or migrate out of the polymer substrate to be protected, or that they are absorbed (chemically or physically) by one or more systems components (such as pigments), thereby diminishing their effectiveness.

Although the presently claimed poly triazine carbamates are not bondable, it is believed that due to their high molecular weight, these triazines will exhibit higher permanence due to reduced volatility and reduced migration within the materials in which they are employed. In particular, it is believed that these triazines will exhibit greater thermal stability than other carbamate containing triazines formed directly from phenolic systems, particularly those in which the carbamate group is bonded directly to the aromatic ring.

EP 434,619 and CA 2,032,669 generically disclose various bondable phenolic carbamoyl triazines and the incorporation of these compounds into polymers by chemical bonding. Additionally, U.S. Pat. No. 5,354,794 discloses generically triazines with one or more carbonyl and/or ester groups. However, the inventors are unaware of any prior art which discloses the novel poly-trisaryl-1,3,5-triazine carbamates of the present invention.

SUMMARY OF THE INVENTION

The present invention provides a new class of trisaryl-1,3,5-triazines which comprise a carbamate triazine polymer. More specifically, the new poly-trisaryl-1,3,5-triazine carbamates of the present invention have the following general formulas (I), (II) and (III):

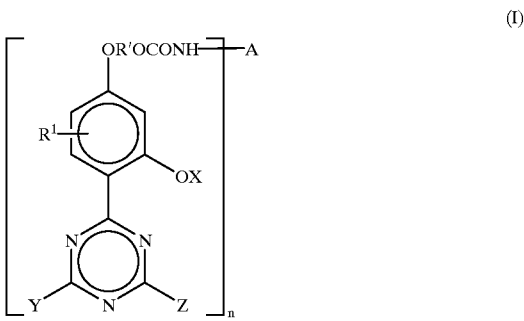

(I)

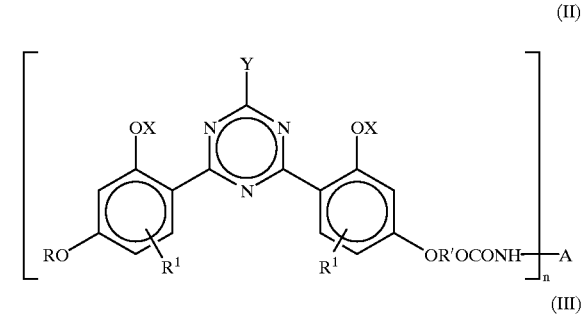

(II)

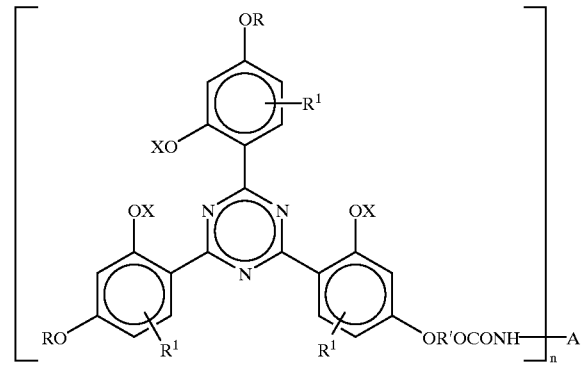

(III)

wherein

A is a polyvalent hydrocarbyl or a heterocyclic ring;

each X is independently selected from hydrogen, allyl, —$COR^a$, —$SO_2R^b$, —$SiR^cR^dR^e$, —$PR^fR^g$, and —$POR^fR^g$;

each of Y and Z are the same or different, and are independently selected from an aryl ring of the general formula (IV);

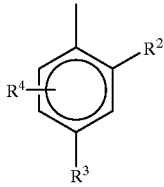

(IV)

each R is independently selected from a hydrocarbyl group, a functional hydrocarbyl group and a hydroxy alkyl amide such as —$CH_2CONC_4H_9(CH_2)_2OH$;

each R' is independently selected from a hydrocarbylene group, a functional hydrocarbylene group and a group such as —$CH_2CONC_4H_9(CH_2)_2$—;

each $R^a$ is independently selected from $C_1$–$C_8$ allyl, halogen-substituted $C_1$–$C_8$ alkyl, $C_5$–$C_{12}$ cycloalkyl, $C_2$–$C_8$ alkenyl, —$CH_2$—$CO$—$CH_3$, $C_7$–$C_{12}$ aralkyl, $C_1$–$C_{12}$ alkoxy, or phenyl which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl, or $C_7$–$C_{18}$ alkylaryl;

each $R^c$, $R^d$, and $R^e$ is independently selected from $C_1$–$C_{18}$ alkyl, cyclohexyl; phenyl, or $C_1$–$C_{18}$ alkoxy;

each $R^f$ and $R^g$ is independently selected from $C_1$–$C_{12}$ alkoxy, phenoxy, $C_1$–$C_{12}$ alkyl, $C_5$–$C_{12}$ cycloalkyl, benzyl, tolyl, or phenyl;

each $R^1$, $R^2$ and $R^4$ is independently selected from hydrogen, hydrocarbyl, functional hydrocarbyl, —O(hydrocarbyl), —O(functional hydrocarbyl), —SR, halogen, —$SO_3R$, —COOR, —COR, —OCOR, —NRR and cyano; and each $R^3$ is independently selected from R, —OR, —SR, halogen, —$SO_3R$, —COOR, —COR, —NRR and cyano.

n is from 2 up to about 50

These poly-trisaryl-1,3,5-triazine carbamate polymers may in general be prepared via a number of procedures described in the previously incorporated references, but preferably by reacting two or more trisaryl-1,3,5-triazine precursors, each having at least one aryl ring with a hydroxyl group ortho to the point of attachment to the triazine ring, such aryl ring being further substituted by a hydroxyl functional —O(hydrocarbyl) group, (and preferably the hydrocarbyl group para to the point of attachment to the triazine ring), with a divalent hydrocarbyl linking agent such as a diisocyanate, or a trivalent hydrocarbyl linking agent such as a triisocyanate to form the compounds of Formulas (I)–(III). Further preferred process details are disclosed below.

The novel poly-trisaryl-1,3,5-triazine carbamates of the present invention are particularly useful as ultraviolet light absorber additives for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, rubbers, paints and other coatings, and adhesives, such as disclosed in a number of the previously incorporated references. The present invention, consequently, also relates to a method for stabilizing a material by incorporating into such material, e.g., organic material, the novel poly-trisaryl-1,3,5-triazine carbamate in an amount effective to stabilize the material against the effects of actinic radiation, and the material so stabilized.

The novel poly-trisaryl-1,3,5-triazine carbamates of the present invention are also effective as ultraviolet light screening agents in applications such as sunscreens and other cosmetic preparations, capstock layers for extruded polymers and laminated UV-screening window films, among others. The present invention, consequently, also relates to a method for screening ultraviolet light from a substrate by applying to such substrate a layer of a composition comprising the novel poly-trisaryl-1,3,5-triazine carbamates, and the substrate so screened.

These and other features and advantages of the present invention will be more readily understood by those of ordinary skill in the art from a reading of the following detailed description.

DETAILED DESCRIPTION OF THE PREFERRED EMBODIMENTS

The Poly-Trisaryl-1,3,5-Triazine Carbamates

As indicated above, the trisaryl-1,3,5-triazines in accordance with the present invention are compounds of the general formulas (I), (II) and (III).

As used herein, the terms "poly-trisaryl-1,3,5-triazine carbamate" or "carbamate triazine" broadly refer to any compound of formulas (I), (II) or (III).

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl, alkylaryl, alkynyl, cycloalkynyl). More specifically, hydrocarbyl includes (but is not limited to) such groups as alkyl, cycloalkyl, aryl, aralkyl, alkylaryl, alkenyl and cycloalkenyl, preferably having up to 24 carbon atoms. A hydrocarbyl may optionally contain a carbonyl group or groups (which is/are included in the carbon count), and/or a heteroatom or heteroatoms (such as at least one oxygen, sulfur, nitrogen or silicon), in the chain or ring.

The term "polyvalent hydrocarbyl" refers to a hydrocarbyl, as defined above, which comprises a polyvalent hydrocarbon group in which the valencies are derived by the abstraction of a hydrogen from different carbon atoms.

The term "functional hydrocarbyl" in the context of the present invention, and in the above formulas, broadly refers to a hydrocarbyl possessing pendant and/or terminal "reactive" and/or "latent reactive" functionality, and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido and activated methylene; isocyanato; cyano; epoxy; and ethylenically unsaturated groups such as allyl, acryloyl and methacryloyl, and maleate and maleimido. Latent reactive functionality refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention, and as would clearly be understood by those persons of ordinary skill in the relevant art, is a substituent attached to the hydrocarbyl chain or ring which during reaction is displaced to create a valency on a carbon atom in the hydrocarbyl chain or ring. As examples of leaving groups may be mentioned halogen atoms such as chlorine, bromine and iodine; hydroxyl groups; quaternary ammonium salts ($NT_4^+$); sulfonium salts ($ST_3^+$); and sulfonates ($-OSO_3T$); where T is, e.g., methyl or para-tolyl. Preferred functionality includes hydroxyl, $-COOR^5$, $-CR^6=CH_2$, $-CO-CR^6=CH_2$, Cl,

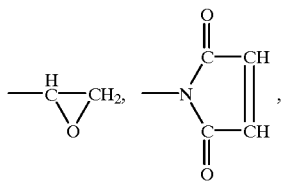

an isocyanate group, a blocked isocyanate group and $-NHR^5$, wherein $R^5$ is selected from hydrogen and a hydrocarbyl (preferably of up to 24 carbon atoms); and $R^6$ is selected from hydrogen and an alkyl of 1 to 4 carbon atoms.

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylaryl, etc.)

The trisaryl-1,3,5-triazines in accordance with the present invention also relate to latent stabilizing compounds against actinic radiation of the general formulas (I), (II) and (III) wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high cleavage rate of the O—X bond and a long shelf life. The use of latent stabilizing compounds is further described in U.S. Pat. Nos. 4,775,707, 5,030,731 and CA A1-2162645.

Latent stabilizing compounds comprising the poly-trisaryl-1,3,5-triazine carbamates in accordance with the present invention can be prepared from compounds of the general formulas (I), (II) and (III) wherein at least one X is hydrogen by subjecting said compounds to a further reaction to form latent stabilizing compounds, as described in U.S. Pat. Nos. 4,775,707 and 5,030,731. For example, acylation can be carried out according to the process described in U.S. Pat. No. 3,249,608, except that excess acylating reagent is preferably employed, to give compounds in which X is $-COR^a$ The reaction to give the latent stabilizing compounds of the present invention of the general formulas (I), (II) and (II) in which X is allyl, $-COR^a$, $-SO_2R^b$, $-SiR^cR^dR^e$, $-PR^fR^g$, or $-POR^fR^g$ can be carried out, for example, by reaction of the compounds of the general formulas (I), (II) and (III) wherein at least one X is hydrogen with the corresponding chlorides: ally chloride, Cl—$COR^a$, Cl—$SO_2R^b$, Cl—$SiR^cR^dR^e$, Cl—$PR^fR^g$, or Cl—$POR^fR^g$. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (I), (II) or (III).

Catalysts customarily used for acylation, sulfonylation, phosphorylation or silylation reactions may be used in forming the latent stabilizing poly-trisaryl-1,3,5-triazine carbamates of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, the R groups are selected a hydrocarbyl group of 1 to 24 carbon atoms; and a functional hydrocarbyl group of 1 to 24 carbon atoms. More preferably, each such R group is independently selected from an alkyl of 1 to 24 carbon atoms (which may optionally be substituted by one or more hydroxyl, carboxyl, carboalkoxy (ester), epoxy, amido and/or amino groups, and/or contain one or more carbonyl groups, oxygen atoms and/or nitrogen atoms in the chain); an alkenyl of 2 to 24 carbon atoms (which may optionally be substituted by hydroxyl, carboxyl, epoxy, amido and/or amino group(s), and/or contain carbonyl, oxygen and/or nitrogen in the chain), a cycloalkyl of 5 to 24 carbon atoms (which may optionally be substituted by hydroxyl, carboxyl and/or amino group(s), and/or contain carbonyl, oxygen and/or nitrogen in the ring), and an aralkyl of 7 to 24 carbon atoms (which may optionally be substituted by hydroxyl, carboxyl and/or amino group(s), and/or contain carbonyl, oxygen and/or nitrogen in the ring).

More preferably, each R group is independently selected from an alkyl of 1 to 24 carbon atoms optionally containing an oxygen atom in the chain, or a hydroxyalkyl of 1 to 24 carbon atoms group optionally containing an oxygen atom in the chain.

In preferred embodiments, the R' groups are selected a hydrocarbylene group of 2 to 24 carbon atoms; and a functional hydrocarbylene group of 2 to 24 carbon atoms. More preferably, each such R' group is independently selected from an alkylene of 2 to 24 carbon atoms (which may optionally be substituted by one or more hydroxyl, carboxyl, carboalkoxy (ester), epoxy, amido and/or amino groups, and/or contain one or more carbonyl groups, oxygen atoms and/or nitrogen atoms in the chain); an alkenyl of 2 to 24 carbon atoms (which may optionally be substituted by hydroxyl, carboxyl, epoxy, amido and/or amino group(s), and/or contain carbonyl, oxygen and/or nitrogen in the chain), a cycloalkylene of 5 to 24 carbon atoms (which may optionally be substituted by hydroxyl, carboxyl and/or amino group(s), and/or contain carbonyl, oxygen and/or nitrogen in the ring), and an aralkylene of 7 to 24 carbon atoms (which may optionally be substituted by hydroxyl, carboxyl and/or amino group(s), and/or contain carbonyl, oxygen and/or nitrogen in the ring).

More preferably, each R' group is independently selected from an alkylene of 2 to 24 carbon atoms optionally containing an oxygen atom in the chain, or a hydroxyalkylene of 2 to 24 carbon atoms group optionally containing an oxygen atom in the chain.

In preferred embodiments, each $R^1$ and $R^4$ is independently selected from hydrogen, an acyl of 2 to 12 carbon atoms, an acyloxy of 2 to 12 carbon atoms, and a hydrocarbyl having from 1 to 12 carbon atoms; more preferably from hydrogen and an alkyl of 1 to 4 carbon atoms; and especially hydrogen.

In preferred embodiments, each $R^2$ is independently selected from hydrogen, a hydrocarbyl group of 1 to 24 carbon atoms, a hydrocarbyloxy group of 1 to 24 carbon atoms, an acyloxy group of 1 to 24 carbon atoms, R and —OR. More preferably, each $R^2$ is independently selected from hydrogen, an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; and an acyloxy group of 2 to 12 carbon atoms. Still more preferably, each $R^2$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain, and an acyloxy of 2 to 12 carbon atoms. Especially preferred is when each $R^2$ is independently selected from hydrogen and an alkyl of 1 to 4 carbon atoms, and particularly hydrogen and methyl.

In preferred embodiments, each $R^3$ is independently selected from hydrogen, a hydrocarbyl group of 1 to 24 carbon atoms, a functional hydrocarbyl group of 1 to 24 carbon atoms, R and —OR. More preferably, each $R^3$ is independently selected from hydrogen, an alkyl of 1 to 24 carbon atoms (which may optionally be substituted by hydroxyl, carboxyl and/or amino group(s), and/or contain carbonyl, oxygen and/or nitrogen in the chain); an alkenyl of 2 to 24 carbon atoms (which may optionally be substituted by hydroxyl, carboxyl and/or amino group(s), and/or contain carbonyl, oxygen and/or nitrogen in the chain); a cycloalkyl of 5 to 12 carbon atoms (which may optionally be substituted by hydroxyl, carboxyl and/or amino group(s), and/or contain carbonyl, oxygen and/or nitrogen in the ring); and —OR. Still more preferably, each $R^3$ is independently selected from hydrogen, an alkyl of 1 to 24 carbon atoms optionally containing an oxygen atom in the chain, a hydroxyalkyl of 1 to 24 carbon atoms group optionally containing an oxygen atom in the chain, and —OR. Especially preferred is when each $R^3$ is independently selected from hydrogen, an alkyl of 1 to 4 carbon atoms and —OR; and particularly hydrogen, methyl and —OR.

In preferred embodiments n is 2 or 3.

As mentioned above, A is a polyvalent hydrocarbyl which comprises a polyvalent hydrocarbon group in which the valencies are derived from the abstraction of a hydrogen from different carbon atoms, or a heterocyclic ring such as a 1,3,5,-triazine. Such hydrocarbyls include aliphatics (straight and branched chain), cycloaliphatics, aromatics and mixed character groups (e.g., aralkyl, alkylaryl, alkynyl, cycloalkynyl). More specifically, hydrocarbyl includes (but is not limited to) such groups as alkyl, cycloalkyl, aryl, aralkyl, alkylaryl, alkenyl and cycloalkenyl, preferably having up to 24 carbon atoms. A hydrocarbyl may optionally contain a carbonyl group or groups (which is/are included in the carbon count), and/or a heteroatom or heteroatoms (such as at least one oxygen, sulfur, nitrogen or silicon), in the chain or ring. A can also be a heterocyclic ring such as a polyvalent 1,3,5-triazine. More preferably, the heterocyclic ring is a di- or trivalent 1,3,5-triazine.

A may also be derived from di- and triisocyanates. Suitable diisocyanates include but are not limited to hexamethylene diisocyanate; dimethyl hexamethylene diisocyanate; trimethyl hexamethylene diisocyanate; metaxylylene diisocyanate; paraxyllylene diisocyanate; tetramethylene diisocyanate; isophorone diisocyanate; para-tetramethylxylene diisocyanate; meta-tetramethylxylene diisocyanate; xylene diisocyanate; para-phenylene diisocyanate and cyclohexyl diisocyanate. Suitable triisocyanates include, but are not limited to isocyanurate trimers of toluene diisocyanate (abbreviated TDI), hexamethylene diisocyanate, or isophorone diisocyanate (IPDE). Other typical triisocyanates are tris-(4isocyanotophenyl)methane and 1,3,5-tris-(6-isocyanatohexyl)biuret. In preferred embodiments, A is:

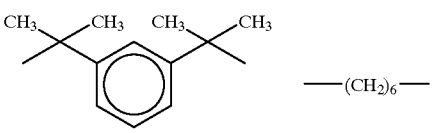

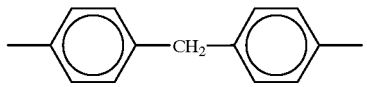

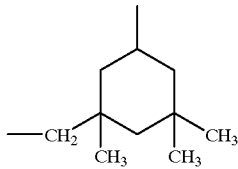

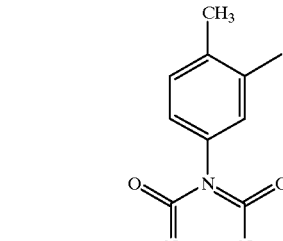

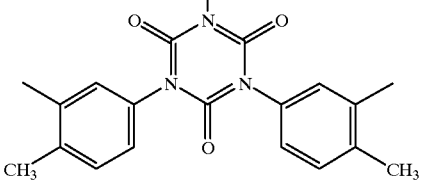

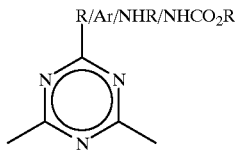

-continued
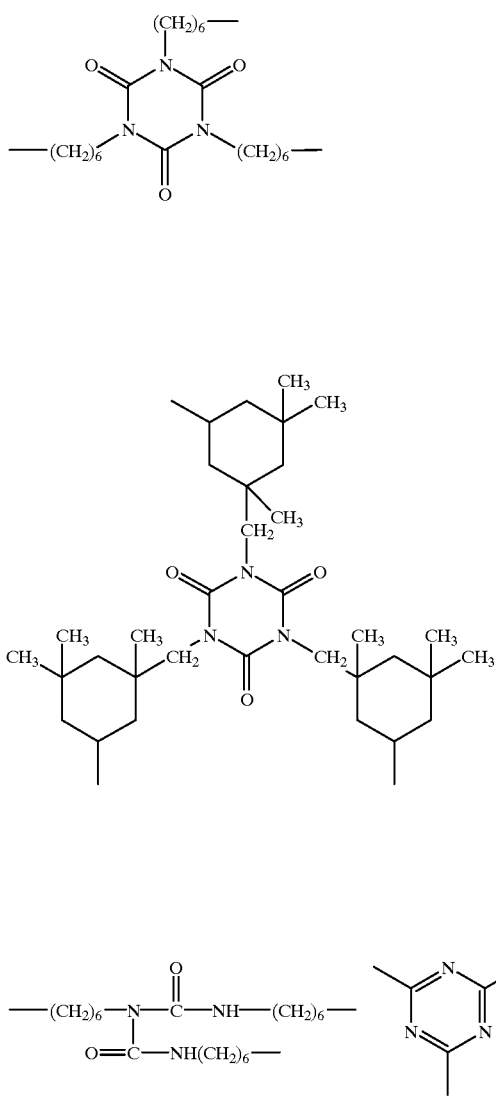
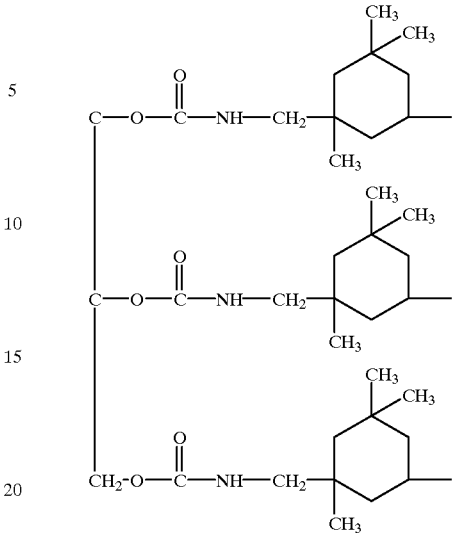
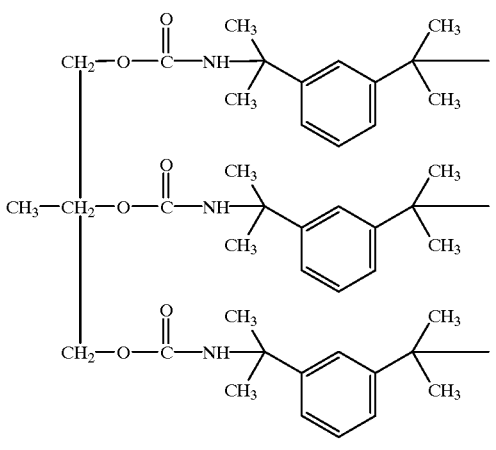
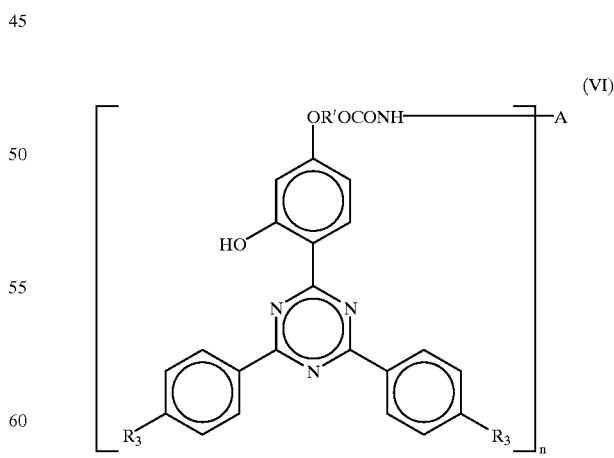
Particularly preferred embodiments of the trisaryl-1,3,5-triazines of the general formula (I) are exemplified by the following structures (V), (VI) and (VII):
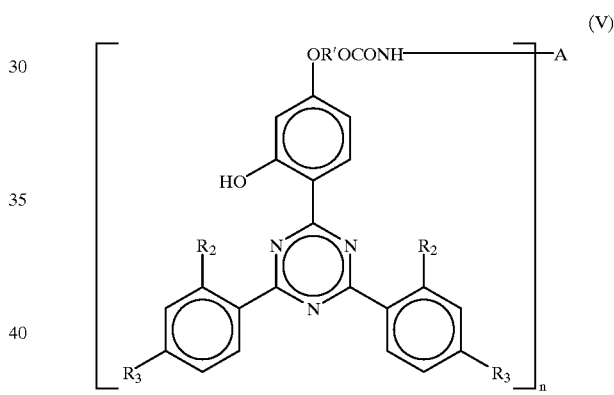

(VII)

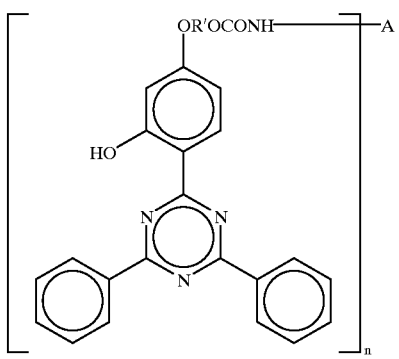

(X)

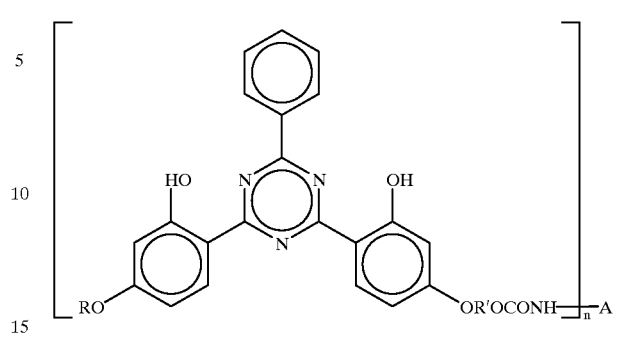

Particularly preferred embodiments of the trisaryl-1,3,5-triazines of the general formula (II) are exemplified by the following structures (VIII), (IX) and (X):

wherein n is 2 or 3.

Particularly preferred embodiments of the trisaryl-1,3,5-triazines of the general formula (III) are exemplified by the following structure (XI):

(VIII)

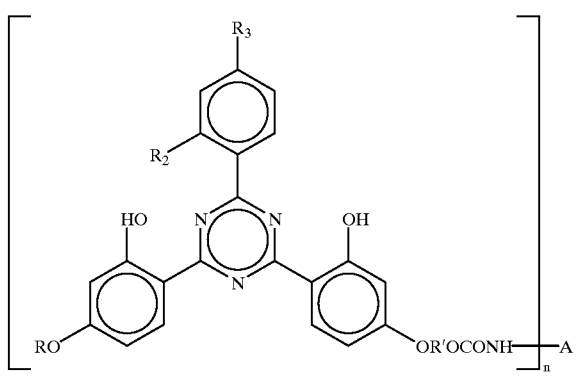

(XI)

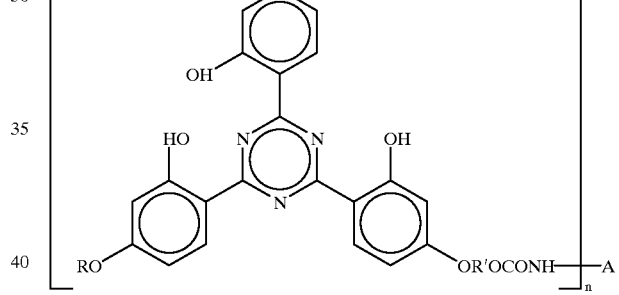

wherein n is 2 or 3.

Methods of Preparation

The poly-trisaryl-1,3,5-triazine carbamates of the present invention can be prepared by a process in which two or more trisaryl 1,3,5,-triazines having an aryl ring containing a hydroxyl group ortho- to the point of attachment to the triazine ring, and further substituted by a hydroxyl functional containing hydrocarbyl group, are reacted using conventional methods including reacting with a polyisocyanate, or by transcarbamoylation with other polycarbamates to produce the carbamate triazine polymers of formulas (I)–(III).

(IX)

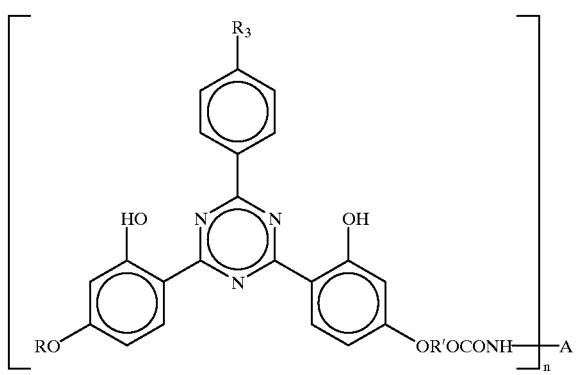

Selection of the triazines suitable for use in synthesizing the triazine carbamates of the present invention is only limited by the requirements that such triazines must contain a hydroxyl group ortho- to the point of attachment to the triazine ring, and a para hydroxyl group which is further substituted by a hydroxyl functional hydrocarbyl group. Suitable triazines include, but are not limited to the following:

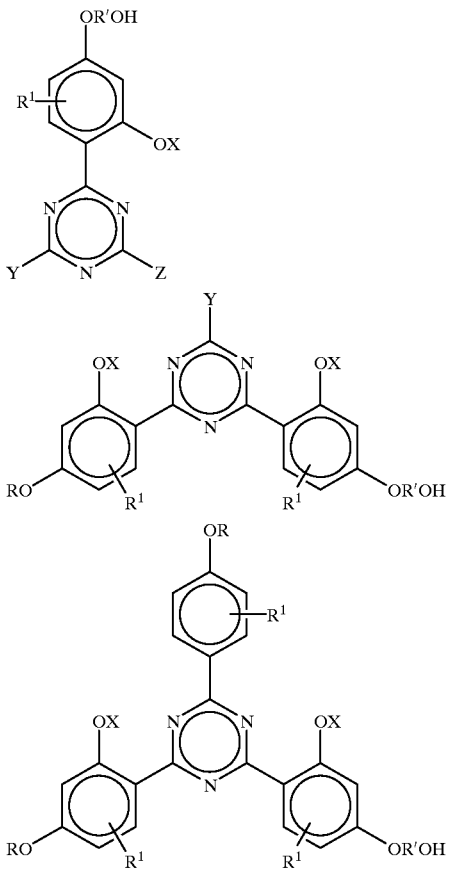

Where R' is a material containing hydroxyl functionality

——(CH$_2$)$_N$OH  N = 1–24

——CH$_2$CH(OH)(CH$_2$)$_3$CH$_3$

——CH$_2$CH(OH)(CH$_2$)$_{11}$CH$_3$

——CH$_2$CH(OH)CH$_2$OC$_4$H$_9$

——CH$_2$CH(OH)CH$_2$OCH—C$_5$H$_{10}$
                              |
                              C$_2$H$_5$

——CH$_2$CH(OH)CH$_2$O(C$_{13}$H$_{27}$ to C$_{15}$H$_{31}$)

——CH$_2$CH(OH)CH$_2$O(C$_{12}$H$_{25}$ to C$_{14}$H$_{29}$)

——CH$_2$CH(OH)CH$_2$OPh

——CH$_2$CH(OH)CH$_2$O—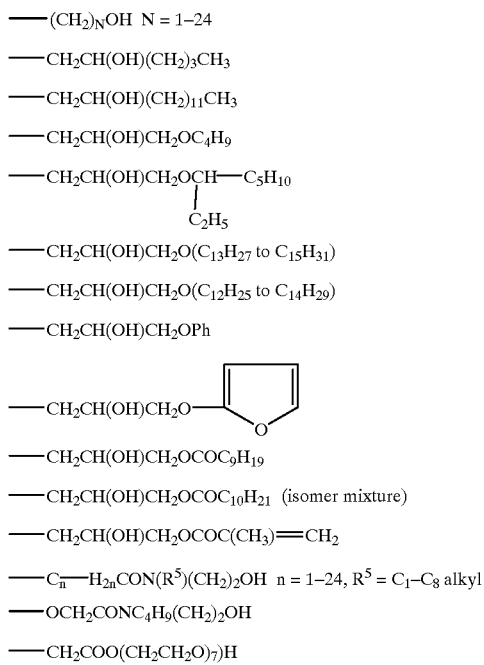

——CH$_2$CH(OH)CH$_2$OCOC$_9$H$_{19}$

——CH$_2$CH(OH)CH$_2$OCOC$_{10}$H$_{21}$  (isomer mixture)

——CH$_2$CH(OH)CH$_2$OCOC(CH$_3$)═CH$_2$

——C$_{\overline{n}}$—H$_{2n}$CON(R$^5$)(CH$_2$)$_2$OH  n = 1–24, R$^5$ = C$_1$–C$_8$ alkyl

——OCH$_2$CONC$_4$H$_9$(CH$_2$)$_2$OH

——CH$_2$COO(CH$_2$CH$_2$O)$_7$)H

-continued

——CH$_2$COOCH$_2$CH(OH)CH$_2$OCOCH═CH$_2$

——CH$_2$COOCH$_2$CH(OH)CH$_2$P(O)(Oc$_4$H$_9$)$_2$

——(CH$_2$CH$_2$O)$_{\overline{m}}$—H  m = 2–9

CH$_3$(CH$_2$)$_7$—CH(OH)—CH—(CH$_2$)$_7$COOC$_8$H$_{17}$

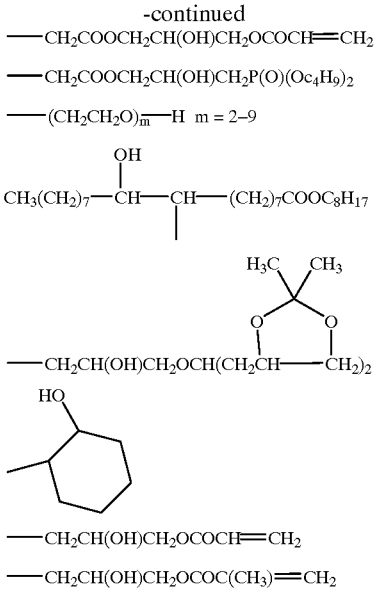

——CH$_2$CH(OH)CH$_2$OCOCH═CH$_2$

——CH$_2$CH(OH)CH$_2$OCOC(CH$_3$)═CH$_2$

Preferred hydroxyl-containing R' groups include —(CH$_2$)$_N$OH (where N=2–6), —CH$_2$CH(OH)CH$_2$O(CH$_2$)$_m$CH$_3$ (where m=3–13), —OCH$_2$CONn—Bu(CH$_2$)OH, Preferably, the divalent hydrocarbyl linking agent is a diisocyanate. Suitable diisocyanates include but are not limited to hexamethylene diisocyanate; dimethyl hexamethylene diisocyanate; trimethyl hexamethylene diisocyanate; metaxylylene diisocyanate; paraxylylene diisocyanate; tetramethylene diisocyanate; isophorone diisocyanate; para-α, α,α',α'-tetramethylxylylene diisocyanate; meta-α,α,α',α'-tetramethylxylene diisocyanate (commercially available under the trade designation m-TMXDI aliphatic isocyanate from Cytec Industries, Inc., West Paterson, N.J.); xylene diisocyanate; para-phenylene diisocyanate and cyclohexyl diisocyanate.

Specific examples of suitable diisocyanates include, but are not limited to, 1-chloro-2,4-phenylene diisocyanate; 2,4-toluene diisocyanate; a mixture of 2,4-toluene and 2,6-toluene diisocyanate; tetramethylphenylene diisocyanate; diphenylmethane-4,4'-diisocyanate; metaphenylene diisocyanate; paraphenylene diisocyanate; 1,5-naphthalene diisocyanate; biphenyl-4,4'-diisocyanate; 4,4'-isopropylidene diphenylisocyanate; benzophenon-4,4'-diisocyanate; diphenylether- and diphenylsulphide diisocyanate; 3.3'-dimethyldiphenyl-4,4'-diisocyanate; 3,3'-dimethoxydiphenyl-4,diisocyanate; 3,3'-dichlorodiphenyl-4,4'-diisocyanate; benzofiuran-2,7-diisocyanate; 4,4'-diphenylmethane diisocyanate; 3,3'-dimethyl-4,4'-biphenylene diisocyanate; 4,4'-dicyclohexylmethane diisocyanate and 1,4-cyclohexane diisocyanate. Additional suitable diisocyanates include hexane 1,6-diisocyanate; 2,2,4-trimethyl-hexane-1,6-diisocyanate; bis-(4-isocyanatocyclohexenyl)methane; ethylene diisocyanate; 1,2-diisocyanatopropane; 3-diisocyanatopropane; 1,2-diisocyanato-cyclohexane; 1,3-diisocyanatocyclohexane; 1,4-diisocyanatobenzene; bis(4-isocyanatocyclohexyl) methane; bis(4-isocyanatophenyl)-methane; 3,3-dichloro-4,4'-diisocyanatobiphenyl; 1,5-diisocyanatonaphthalene; hydrogenated toluene diisocyanate; 2,2'-diisocyanatodiethyl fumarate; 1,5-diisocyanato-1-carboxypentane; 1,2-,1,3-,1,6-,1,7-,1,8-,2,7- and 2,3-diisocyanato-naphthalene; 2,4- and 2,7-diisocyanato-1-methylnaphthalene; 4,4'-diisocyanatobiphenyl; 4,4'-diisocyanato-3,3'- diisocyanato- 6(7)-methylnaphthalene; 4,4'-diisocyanato-2,2'-dimethylbiphenyl; bis-(4-isocyanatophenyl)ethane and bis (4-isocyanatophenyl) ether.

Preferred diisocyanates include meta-α,α,α',α'-tetramethylxylylene diisocyanate (m-TMXDI®), hexane 1,6-diisocyanate (also known as hexamethylene diisocyanate, abbreviated HDI, bis-(4-isocyanatocyclohexyl)methane, and 1-isocyanato-3,3,5-trimethyl-5-isocyanatomethyl cyclohexane (isophorone diisocyanate, abbreviated IPDI).

In addition to carbamate dimers derived from diisocyanates, this invention encompasses carbamate trimers derived from triisocyanates. Typical triisocyanates are isocyanurate trimers of toluene diisocyanate (abbreviated TDI), hexamethylene diisocyanate, or isophorone diisocyanate (IPDI). These trimers are characterized by the 1,3,5-triazine-2,4,6-(1H,3H 5H)-trione ring. Other typical triisocyanates are tris-(4-isocyanatophenyl)methane and 1,3,5-tris-(6-isocyanatohexyl)biuret. An example of a heterocyclic triisocyanate is 2,4,6-triisocyanato-1,3,5-triazine.

This invention also encompasses carbamate triazines obtained by reaction of hydroxyl functional triazines with the reaction products of diisocyanates with polyols, for example, ethylene glycol, propylene glycol, neopentyl glycol, trimethylolpropane, pentaerythritol and the like, as well as oligomeric and polymeric polyols. Preferred examples are diisocyanate/trimethylolpropane adducts. Especially preferred examples are the 3:1 meta-α,α,α',α'-tetramethylxylylene diisocyanate (m-TMXDI®)/trimethylolpropane adduct commercially available under the trade designation Cythane® 3160 Aliphatic Polyisocyanate (Cytec Industries, Inc.) and the 3:1 IPDI/trimethylolpropane adduct commercially available under the trade designation Spenlite® P25-A4-60 aliphatic urethane prepolymer (Reichhold Chemicals, Research Triangle Park, N.C.).

In addition to carbamate dimers derived from diisocyanates, and carbamate trimers derived from triisocyanates, there are a number of other modified polyisocyanate precursors. Examples of modified polyisocyanate precursors are:

(a) the polymethylene polyphenylene ester of isocyanic acid (polymethylene polyphenylene polyisocyanate);

(b) copolymers of meta-isopropenyl-α,α'-dimethylbenzyl isocyanate (commercially available from Cytec Industries, Inc. under the trade designation m-TMI®) and vinyl monomers (e.g. ethyl acrylate, butyl acrylate, methyl methacrylate styrene, and α-methyl styrene);

(c) the reaction product of diphenylmethane diisocyanate (abbreviated MDI) and low molecular weight polyether diols (e.g. Luprante® MP102, BASF Wyandotte Corp.);

(d) the reaction product of diphenylmethane diisocyanate (abbreviated MDI) and low molecular weight polyester diols (e.g. Baytec® MS-242, Mobay Corp.);

(e) the reaction product of IPDI dimer and a polyol (e.g. IPDI-BF 1540, Nuodex®);

(f) the reaction product of toluene diisocyanate (abbreviated TDI) trimer and phenol (Desmodur® CT Stabil, Mobay Corp.);

(g) the uretoneimine of MDI (Lupranate® MM 103, BASF Wyandotte Corp.).

Preferred examples of carbamates used in the transcarbamoylation reaction are 2,4,6-trisalkoxy carbamoylamino 1,3,5-triazine, 2,4,6-trisphenoxy carbamoylamino-1,3,5-triazine and triazine isocyanate.

Uses of the Poly-Trisaryl-1,3,5-Triazine Carbamates

As indicated earlier, the novel poly-trisaryl-1,3,5-triazine carbamates of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The novel poly-trisaryl-1,3,5,triazine carbamates of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the poly-trisaryl-1,3,5-triazine carbamates of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfides, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

Further non-limiting examples of specific polymers which may be stabilized include:

1. Homo-, copolymers and terpolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE), polypropylene, syndiotactic polypropylene, isotactic polypropylene, ethylene-propylene(EP), et-prop-dicyclopentadiene and (EPDM)terpolymer. Further examples are all of the above said polymers wherein a metallocene catalyst is used in preparation, blends thereof, and copolymers and terpolymers with other unsaturated monomers.

2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.

3. Hydrocarbon resins (such as $C_5$–$C_9$) including hydrogenated modifications thereof and mixtures of polyalkylenes and starch.

4. Homo- and copolymers of styrenes such as styrene, p-methylstyrene and α-methylstyrene.

5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.

6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.

7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.

8. Homo- and copolymers derived from α,β-unsaturated acids and derivatives thereof such as acrylic acid, methacrylic acid, acrylates, methacrylates, acrylamides and acrylonitriles.

9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.

10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above. For the preceding groups 1–10 of polymers, the present invention further encompasses these polymers as prepared by metallocene catalysts.

11. Homo- and copolymers of cyclic ethers such as alkylene glycols and alkylene oxides, as well as copolymers with bisglycidyl ethers.

12. Polyacetals such as polyoxymethylene and those polyoxymethylenes which contain ethylene oxide as a comonomer; and polyoxymethylenes modified with thermoplastic polyurethanes, acrylates and/or MBS.

13. Polyphenylene oxides and sulfides.

14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.

15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).

16. Polyureas, polyimides, polyamideimides, polyetherimides, polyesterimides, polyhydantoins and polybenzimidazoles.

17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.

18. Polycarbonates and polyester carbonates.

19. Polysulfones, polyether sulfones and polyether ketones.

20. Crosslinked polymers derived from aldehydes condensation resins such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents and also halogen-containing modifications thereof.

23. Crosslinkable acrylic resins derived from substituted acrylates such as epoxy acrylates, hydroxy acrylates, isocyanato acrylates, urethane acrylates or polyester acrylates.

24. Alkyd resins, polyester resins and acrylate resins crosslinked with melamine resins, urea resins, isocyanates, isocyanurates, carbamates or epoxy resins.

25. Crosslinked epoxy resins derived from aliphatic, cycloaliphatic, heterocyclic and/or aromatic glycidyl compounds such as bisphenol A and bisphenol F, which are crosslinked with hardeners such as anhydrides or amines.

26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.

27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PATENT/HDPE, PP/HDPE, PP/LDPE, LDPE/HDPE, LDPE/EVA, LDPE/EAA, PATENT/PP, PATENT/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin. Other materials which can be stabilized include, for example:
33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

Aliphatic Polyamide

The novel poly-trisaryl-1,3,5-triazine carbamates of the present invention can also be used with aliphatic polyamide polymers. An "Aliphatic polyamide" is a polyamide characterized by the presence of recurring carbonamide groups as an integral part of the polymer chain which are separated from one another by at least two aliphatic carbon atoms. Illustrative of these polyamides are those having recurring monomeric units represented by the general formula:

—NHC(O)RC(O)NHR$^1$— or —NH—R—C(O)— or a combination hereof in which R and R' are the same or different and are alkylene groups of at least about two carbon atoms, preferably alkylene having from about 2 to about 12 carbon atoms. Exemplary of such polyamides are polyamides formed by the reaction of diamines and diacids such as poly (tetramethylene adipamide)(nylon 4,6); poly (hexamethylene adipamide) (nylon 6,6); poly hexamethylene azelamide) (nylon 6,9); poly(hexamethylene sebacamide) (nylon 6,10); poly(heptamethylene pimelamide) (nylon 8,8); poly(nonamethylene azelamide) (nylon 9,9); poly(decamethylene azelamide) (nylon 10,9); and the like. Also illustrative of useful aliphatic polyamides are those formed by polymerization of amino acids and derivatives thereof, as for example lactams. Illustrative of these useful polyamides are poly(4-aminobutyric acid) (nylon 4); poly(6-aminohexanoic acid) (nylon 6); poly(7-aminoheptanoic acid) (nylon 7); poly(8-aminoocatanoic acid) (nylon 8); poly(9aminononanoic acid) (nylon 9); poly(10-aminodecanoic acid) (nylon 10); poly(11-aminoundecanoic acid) (nylon 11); poly(12-aminododecanoic acid) (nylon 12); and the like. Blends of two or more aliphatic polyamides may also be employed.

Copolymers formed from any combination of the recurring units of the above referenced aliphatic polyamides can be used. By way of illustration and not limitation, such aliphatic polyamide copolymers include caprolactam/hexamethylene adipamide copolymer (nylon 6/6,6); hexamethylene adipamide/caprolactam copolymer (nylon 6, 6/6); hexamethylene adipamide/hexamethylene-azelamide copolymer (nylon 6,6/6,9); and copolymers formed from recurring units of the above referenced aliphatic polyamides with aliphatic/aromatic polyamide recurring units may also be used. Examples of such copolyamides are nylon 6/6T; nylon 6,6/6, T; nylon 6/10T; nylon 6/12T; nylon 6,10/6,T etc.

Preferred aliphatic polyamides for use in the practice of this invention are poly(caprolactam); poly(7-aminoheptanic acid); poly(tetramethylene adipamide); poly(hexamethylene adipamide); and mixtures thereof. The particularly preferred aliphatic polyamides are poly(caprolatam); poly (hexamethylene adipamide); poly(tetramethylene adipamide); and mixtures thereof.

Aliphatic polyamides useful in the practice of this invention may be obtained from commercial sources or prepared in accordance with known preparatory techniques. For example, polycaprolactam may be obtained from Allied Signal Inc. and poly(hexamethylene adipamide) may be obtained from DuPont Co.

The number average molecular weight of the aliphatic polyamide may vary widely. Usually, the aliphatic polyamide is of film forming molecular weight that is sufficiently high to form a free standing film and sufficiently low to allow melt processing of the blend into a film. Such number average molecular weights are well known to those of skill in the film art and are usually at least about 5,000 as determined by the formic acid viscosity method. In this method, a solution of 9.2 wt. Concentration of aliphatic polyamide in 90% formic acid at 25° C. is used. In the preferred embodiments of the invention, the number average molecular weight of the aliphatic polyamide is from about 5,000 to about 1,000,000 and in the particularly preferred embodiments is from about 10,000 to about 100,000. Amongst the particularly preferred embodiments, most preferred are those in which the molecular weight of the aliphatic polyamide is from about 20,000 to about 40,000.

Polyurethane

Polyurethane (PUR) elastomer products ("spandex") can be stabilized against discoloration and loss of elasticity during UV light exposure with combinations of UV absorbers according to the invention and hindered amine light stabilizers. Spandex fibers is a PUR elastomer product, which requires very specific UV absorber and hindered amine light stabilizers properties in order to achieve optimum performance. UV absorbers of the triazine class of this invention can be combined with polymeric hindered amine light stabilizers (HALS) to provide outstanding performance in achieving the desired properties for the Spandex fiber applications.

The triazine UV absorber of the invention, used alone or in combination with HALS provides the following properties in the Spandex fiber application: (1) low color contribution at typical use levels in the 0.5–2.0% range; (2) sufficient MW, thermal stability and low volatility for fiber processing and thermal exposure conditions; (3) high compatibility and permanence; (4) prevent discoloration and loss of elasticity during exposure to UV light energy; (5) low extraction by water and dry cleaning solvents; (6) low color development during exposure to atmospheric pollutants, $NO_x$, $SO_x$, hydrocarbons, etc.; (7) low interaction with sea water and pool chemicals; (8) low interaction and color development with typical phenolic antioxidants used for the thermal stabilization of Spandex fibers; and (9) low interaction with copper based antioxidant systems used in Nylon fibers for Nylon/Spandex fabrics.

The triazine UV absorber with or without the polymeric HALS provides outstanding stabilization with minimum negative effect on secondary performance properties, such as low color development during $NO_x$ exposure and low interaction with copper based antioxidant systems using in Nylon fibers.

As noted above, any of the triazine compounds disclosed herein can be used to impart one or more of the properties described above to Spandex fibers when added thereto in a stabilization effective amount.

Preferably, these triazine compounds are added in combination with polymeric HALS. The polymeric HALS is preferably poly[(6-morpholino-s-triazine-2,4-diyl)[2,2,6,6,-tetramethyl-4-piperidyl)imino]-hexamethylene [(2,2,6,6-tetramethyl-4-piperidyl)imino]]. Most preferably, the polymeric HALS is the methylated (M) version of the above HALS, which is sold by Cytec Industries, Inc. as CYASORB®UV-3529 light stabilizer. Other polymeric HALS disclosed in U.S. Pat. No. 4,331,586 are also suitable.

Spandex fibers are made from a polyurethane (PUR) prepolymer prepared from a diisocyanate and a glycol. There are four basic processes used to convert the PUR prepolymer into the fiber product. These processes are Solution Dry Spinning, Solution Wet Spinning, Melt Extrusion, and Reaction Spinning. The above UV stabilizer alone or in combination with HALS would be suitable for use in any or all four processes.

Spandex fibers may contain a processing antioxidant system, such as a phenolic antioxidant, or a phenolic/phosphite antioxidant combination. In addition, pigments, such as $TiO_2$ are commonly used in the fiber products.

The triazine UV absorber alone or with M-HALS can be dissolved into DMF or DMAC and added to the PUR prepolymer solution prior to solution fiber spinning processes. Also, the combination can be extrusion compounded into the PUR compound used in the melt spinning process.

Polycarbonates

Among polymeric compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

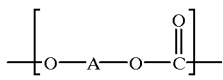

wherein A is a divalent phenolic radical. Examples of A are given inter alia in U.S. Pat. No. 4,960,863 and DE-A-3 922,496. A can be derived, for example, from hydroquinone, resorcinol, dihydroxybiphenylene or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)propane, 2,2-bis(3,5-dichloro-4-hydroxyphenyl)p 1,1-bis(4-hydroxyphenyl)cyclohexane, or from the compounds of the formulae:

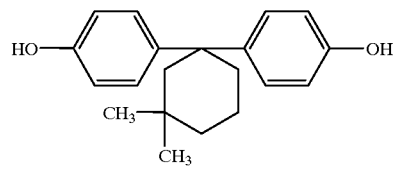

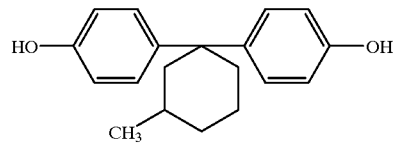

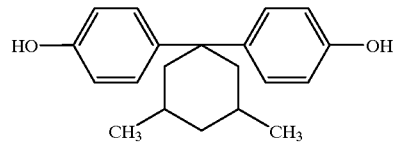

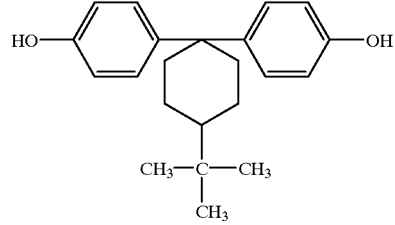

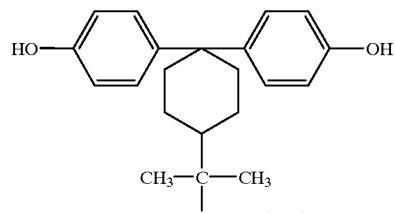

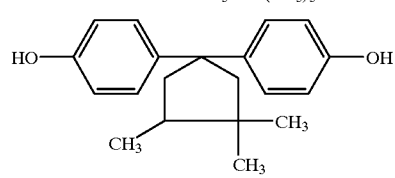

-continued

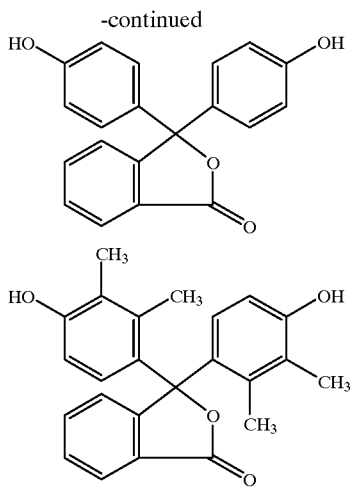

In one embodiment, the preferred resins are polycarbonates based on dihydric phenols such as 2,2-bis-(4-hydroxyphenyl)propane (bisphenol A); 2,4-bis (4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane.

Also preferred are polycarbonate copolymers incorporating two or more phenols, branched polycarbonates wherein a polyfunctional aromatic compounds is reacted with the dihydric phenol(s) and carbonate precursor, and polymer blends of which polycarbonate comprises a significant portion of the blend.

The most preferred resins for both layers are polycarbonates based on bisphenol A.

U.S. Pat. No. 5,288,788 also describes polycarbonates and polyester carbonates, especially aromatic polycarbonates, for example those based on 2,2-bis(4-hydroxyphenyl) propane or 1,1-bis(4-hydroxyphenyl)cyclohexane.

British Patent Appn. No. 2,290,745 describes a number of methods have been developed to concentrate UV absorbers near or at the surface of polymeric materials. These include surface impregnation (see U.S. Pat. Nos. 3,309,220, 3,043, 709, 4,481,664 and 4,937,026) and coating a plastic article with solutions containing thermoplastic resins and UV absorbers (see U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557,265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

In one embodiment, the invention also relates to thermoplastic articles coated with a thermoplastic layer 0.1 to 10 mil (0.00254 mm to 0.254 mm), preferable 0.1 to 5 mil (0.00254 mm to 0.127 mm), thick, in which said layer contains 0.1% to 20% by weight of the poly-trisaryl-1,3,5-triazine carbamates of the present invention. Preferred concentrations of are 2% to 15% by weight; most preferred concentrations of 5% to 10% by weight.

The poly-trisaryl-1,3,5-triazine carbamates of the present invention may be incorporated into the thermoplastics of the surfaces layer by standard methods such as dry mixing the additives with granular resin prior to extruding.

The poly-trisaryl-1,3,5-triazine carbamate containing layer may be applied to one or both sides of the thermoplastic article.

Laminated thermoplastic articles which contain additional layers such as a water resistant layer as found in U.S. Pat. No. 4,992,322 are also part of the present invention.

The core layer and the coating layer may be of the same thermoplastic resin or different thermoplastic polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride.

Mixtures (polyblends) of such polymers with one another or with other polymers, for example with polyolefins, polyacrylates, polydienes or other elastomers in the form of impact strength modifiers.

The poly-trisaryl-1,3,5-triazine carbamates of the present invention can also be chemically bonded to substrates, such as polymers, thereby greatly reducing the migration of such UV absorbers, e.g., out of the substrate or away from the substrate surface. The bonding mechanism of the triazines of the present invention involves the formation of a bond (chemical and/or co-valent) between a functionality attached to the amido or carbamate group, e.g., by a pendant vinyl or hydroxyl group, and the "host" substrate, such as a polymer.

Incorporation of the poly-trisaryl-1,3,5-triazine carbamates of the invention can be brought about by copolymerization, copolyaddition, copolycondensation, by reaction with a polymer which carries suitable functional groups, or by grafting, in a manner as disclosed in U.S. Pat. Nos. 3,423,360 and 5,189,084 which are incorporated herein by reference as if fully set forth.

Bonding of the poly-trisaryl-1,3,5-triazine carbamates of the invention can occur by polymerization or copolymerization. In the case of the novel triazines of the present invention comprising pendant vinyl groups, polymerization or copolymerization with at least one vinyl monomer, e.g., (meth)acrylic acid, esters of (meth)acrylic acid such as methyl acrylate, amides of (meth)acrylic acid, hydroxyethylacrylate, olefins, vinyl chloride, styrene, butadiene, isoprene and acrylonitrile can be carried out to form homopolymers or copolymers in which the vinyl group is incorporated into the backbone of the polymer. Polymerization or copolymerization can be initiated by initiators, such as free radical, anionic and cationic types, or by actinic radiation, such as UV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

Also, bonding of the presently claimed poly-trisaryl-1,3, 5-triazine carbamate compounds of the present invention can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (I)–(V) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (I)–(V) can be bonded to a monomeric component which is then incorporated into a polymer or copolymer, e.g., by the free radical initiated addition or copolycondensation methods described above. Analogous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the poly-trisaryl-1,3,5-triazine carbamates of the invention may also be bonded to polymers by reaction with an oligomer and/or polymer which carries suitable functional groups. For example, at least one triazine compound comprising a vinyl pendant group can be added, optionally with at least one other vinyl monomer or compound comprising a vinyl group, to unsaturated polyester resins, unsaturated polybutadiene oligomers or unsaturated rubbers and then cured by actinic radiation or by a free radical catalyst. Or, at least one triazine compound comprising a terminal functional group, such as hydroxyl or amido, may be reacted with a polymer and/or oligomer such as polyesters, polyurethanes and polydiols with reactive end-groups, partially hydrolyzed polyvinylacetate, epoxy resins, polysiloxanes and polymers comprising maleic anhydride, either in the main chain or as a side-chain, by methods analogous to those well known to those of ordinary skill in the art Grafting is yet another way of bonding of the presently claimed poly-trisaryl-1,3,5-triazine carbamates to polymers and/or oligomers. Grafting may be carried out in solution, in the melt, or in the solid state with the initiators or actinic radiation types discussed above for polymerization when, for example, the novel triazines of the present invention comprising pendant vinyl groups are used. Such poly-trisaryl-1,3,5-triazine carbamates may be grafted to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(diene monomer) terpolymers and polystyrene and its copolymers.

The poly-trisaryl-1,3,5-triazine carbamates of the present invention may be used in widely varying amounts in such applications depending upon such things as the material to be stabilized and the particular application. However, when employed as a stabilizing additive for materials such as organic polymers, the poly-trisaryl-1,3,5-triazine carbamates of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines are utilized in the same relative amounts but based on the total weight of the screening agent.

The novel stabilizers of the present invention may also be employed in a non-bondable capacity, for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the novel poly-trisaryl-1,3,5-triazine carbamate compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the poly-trisaryl-1,3,5-triazine carbamates of the present invention may be combined with a variety of additives conventionally employed in the UV stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl) phenol; 2,4-dimethyl-6-(1-methylheptadec-1-yl)phenol; 2,4-dimethyl-6-(1-methyltridec-1-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as α-tocopherol, β-tocopherol, γ-tocopherol, δ-tocopherol, and mixtures thereof (vitamin E).

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols such as 2,2'-methylenebis(&tert-butyl-4-methylphenol); 2,2'-methylenebis(6-tert-butyl-4-ethylphenol); 2,2'-methylenebis[4-methyl-6-(α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbezyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O—, N— and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xv) Esters of α-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

(xvii) Amides of β-(3,5-di-tert-butyl-4hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p- phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; allyldiphenylamine; 4-isopropoxydiphenylamine; -phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl)amine; 2,6-di-tert-butyl-4dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl)amino]ethane; 1,2-bis(phenylamino)propane; (o-tolyl)biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl4H-1,4-benzothiazine; phenothiazine; a mixture of mono- and dialkylated tert-butyl/tert-octyl phenothiazines; a mixture of mono and dialkylated tert-octylphenothiazines; N-allylphenothiazine; N,N,N'N'-tetraphenyl-1,4-diaminobut-2-ene; N,N-bis(2,2,6,6-tetramethylpiperid-4-yl)hexamethylenediamine; bis(2,2,6,6-tetrainethylpiperid-4-yl)sebacate; 2,2,6,6-tetramethylpiperidin-4-one; and 2,2,6,6-tetramethylpiperidin-4-ol.

b. UV-absorbers and Light Stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole 2-(3',5'-di-tert-amyl-2'-hydroxphenyl)benzotriazole; 2-(3',5'bis(α,α-dimethylbenzyl)2'hydroxyphenyl)benzotriazole; a mixture of 2-(3'-tert-butyl-2'-hydroxy-5'-(2octyloxycarbonylethyl)phenyl)-5-chloro-benzotriazole, 2-(3'-tert-butyl-5'-[2-(2-ethylehexyloxy)-carbonylethyl]-2'-hydroxphenyl)-5-chloro-benzotriazole, 2-(3'-tert-butyl-2'-hydroxy-5'-(2-methoxycarbonylethyl)phenyl)5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2isooctyloxycarbonylethyl)phenylbenzotriazole; 2,2-methylenebis[4-(1,1,3,3-tetramethylbutyl)-6-benzotriazol-2ylphenol]; the transesterification product of 2-[3'-tert-butyl-5'-(2-methoxycarbonylethyl)-2'-hydroxyphenyl]benzotriazole with polyethylene glycol 300; and [R—CH$_2$CH—COO(CH2)$_3$]$_2$ B where R=3'-tert-butyl-4'-hydroxy-5'-2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl α-cyano-β,β-diphenylacrylate; isooctyl α-cyano-β,β-diphenylacrylate; methyl α-carbomethoxycinnamate; methyl α-cyano-β-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramnethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2,2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl) hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4dione; 3-dodecyl-1-(2,2,6,6-tetramethylpiperidin-4 -yl) pyrrolidin-2,5-dione; 3-dodecyl-1-(1-ethanoyl-2,2,6,6-tetramethylpiperidin-4-yl)pyrrolidin-2,5-dione;

3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl),1,3,5-triazine; 2-(2-hydroxy-4-(mixed iso-octyloxyphenyl))-4,6-bis (2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5- triazine; 2-(2-hydroxy-4-dodecyloxyphenyl)-4,6-bis(2,4-methylphenyl)-1,3,5-triazine; 2-(2-hydroxy-4-tridecyloxyphenyl)-4,6-bis(2,4-dimethylphenyl)-1,3,5-triazine; 2-[2-hydroxy4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tis[2-hydroxy-4-(3-butoxy-2-hydroxypropoxy) phenyl]-1,3,5-triazine; and 2-(2-hydroxyphenyl)-4-(4-methoxyphenyl)-6phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl)pentaerythirtol diphosphite; bis(2,6-di-tert-butyl-4-methylphenyl) pentaerythritol diphosphite; bis(isodecyloxy)pentaerythritol diphosphite; bis(2,4-di-tert-butyl-6-methylphenyl) pentaerythritol diphosphite; bis(2,4,6-tris(tert-butyl)phenyl) pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methlylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers (e.g., ionomers).

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. Nos. 4,325,863, 4,338,244, 5,175,312, 5,216,052, 5,252,643, DE-A-4316611, DE-A-4316622, DE-A4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The novel poly-trisaryl-1,3,5-triazine carbamates of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 µm thick and, preferably, about 10–100 µm thick) to a shaped article made from a polymer containing little or no ultraviolet stabilizers. Such composition may be applied at the same time as the shaping of the base structure, for example by coextrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the poly-trisaryl-1,3,5-triazine carbamate compounds of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel mixtures comprising compounds of the formulas (I)–(V) can be used as stabilizers for coatings, for example for paints such as disclosed in numerous references (see, e.g., U.S. Pat. Nos. 4,619,956, 4,740,542, 4,826,978, 4,962,142, 5,106,891, 5,198,498, 5,298,067, 5,322,868, 5,354,794, 5,369,140, 5,420,204, 5,461,151, 5,476,937, EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the presently claimed poly-trisaryl-1,3,5-triazine carbamates of the present invention.

Multilayer systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The binder can in principle be any binder which is customary in industry, for example those described in Ullmann's Encyclopedia of Industrial Chemistry, 5th Edition, Vol. A18, pp. 368–426, VCH, Weinheim 1991 which is incorporated herein by reference. In general, it is a film-forming binder based on a thermoplastic or curable resin, predominantly on a curable resin. Examples of thermoplastic binders include acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991. Preferred binders include those which comprise a functional acrylate resin and a crosslinking agent.

A wide variety of binders may be employed in such coating systems. Examples of suitable coating compositions containing specific binders include but are not limited to:

1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

In addition to the binder and novel poly-trisaryl-1,3,5-triazine carbamates of the present invention, the coating composition according to the invention preferably further comprise one or more additional ultraviolet light absorbers, including but not limited to those specifically listed above in section b. The additional UV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to amido or carbamate triazine is 4:1 to 1:4. More preferably, the weight ratio of benzotriazole to amido or carbamate triazine is 2:1 to 1:2.

To achieve maximum light stability, it is of particular interest to add sterically hindered amines, examples of which are set out in the above-mentioned section b(vi). The invention therefore also relates to a coating composition which, in addition to the binder, the novel poly-trisaryl-1,3,5-triazine carbamates and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

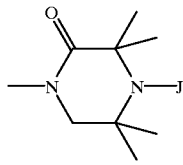

in which J is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

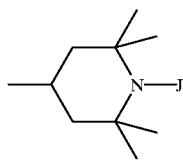

in which J is, for example, hydrogen, hydroxyl, allyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933, 4,344,876, 4,426,471, 4,426,472, 4,619,956, 5,004,770, 5,006,577, 5,064,883, 5,112,890, 5,124,378, 5,106,891, 5,204,473, and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):
bis(2,2,6,6-tetramethylpiperid-4-yl) succinate,
bis(2,2,6,6-tetramethylpiperid-4-yl) sebacate,
bis(1,2,2,6,6-pentamethylpiperid-4-yl) sebacate,
di(1,2,2,6,6-pentamethylpiperid-4-yl) butyl-(3,5-di-tert-butyl-4-hydroxybenzyl)malonate,
bis(1-octyloxy-2,2,6,6-tetramethylpiperid-4-yl) sebacate,
tetra(2,2,6,6-tetramethylpiperid4-yl) butane-1,2,3,4-tetracarboxylate, tetra(1,2,2,6,6-pentamethylpiperid-4-yl) butane-1,2,3,4-tetracarboxylate, 2,2,4,4-tetramethyl-7-oxa-3,20-diaza-2 1-oxo-dispiro[5.1.11.2]heneicosane, and 8-acetyl-3-dodecyl-1,3,8-triaza-7,7,9,9-tetramethylspiro[4.5]decane-2,4-dione. Commercially available examples of these and other tetraalkylpiperidine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASORB® UV-3346, UV 3529, UV-3853, UV-500 and UV-516 (Cytec Industries Inc.).

Apart from the binder, the poly-trisaryl-1,3,5-triazine carbamates, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Possible drying catalysts or curing catalysts are, for example, organometallic compounds, amines, acids, amino-containing resins and/or phosphines.

Examples of acid catalysts are mineral acids, aliphatic and aromatic sulfonic acids (e.g. p-toluene sulfonic acid, dinonylnaphthalene disulfonic acid, dodecylbenzene sulfonic acid), oxalic acid, maleic acid, hexamic acid, phosphoric acid, alkyl phosphate esters, phthalic acid and acrylic acid copolymers.

Examples of organometallic compounds are metal carboxylates, especially those of the metals Pb, Mn, Co, Zn, Zr or Cu, or metal chelates, especially those of the metal Al, It or Zr, or organometallic compounds such as organotin compounds, for example. Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. Al 8, pages 451–453. In radiation-curable coating compositions, the novel stabilizers can also be employed without the addition of sterically hindered amines.

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. Thermosetting coatings are preferably cured at 50–150° C. and, in the case of powder coatings, even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formulas (I)–(V), according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof; and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a compound of a poly-trisaryl-1,3,5-triazine carbamates and to the use of mixtures comprising poly-trisaryl-1,3,5-triazine carbamate compound in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The poly-trisaryl-1,3,5-triazine carbamates of this invention may be applied topically by polishing a surface with a composition comprising the poly-trisaryl-1,3,5-triazine carbamate and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel poly-trisaryl-1,3,5-triazine carbamate compounds in photographic materials as stabilizer against damage by light, especially by UV light. The invention therefore also relates to a photographic material comprising an poly-trisaryl-1,3,5-triazine carbamate compound.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. Nos. 4,853,471, 4,973, 702, 4,921,966 and 4,973,701), benzophenones, oxanilides, cyanoacrylates, salicylates, or acrylonitriles or thiazolines. In this context it is advantageous to employ these further, oil-dissolved UV absorbers in the photographic material in layers other than those comprising the novel UV absorbers.

The present invention also encompasses compositions containing one or more binders. In particular, the binder may comprise an alkyd, acrylic, polyester, phenolic, melamine, epoxy or polyurethane resin, or blends thereof. Examples of such binders include, but are not limited to:

(a) cold- or hot-crosslinkable alkyd, acrylate, polyester, epoxy or melamine resins or mixtures of such resins;

(b) a two-component polyurethane system comprising hydroxyl-containing acrylate, polyester or polyether resins and aliphatic or aromatic isocyanates, isocyanurates or polyisocyanates;

(c) a one-component polyurethane system comprising blocked isocyanates, isocyanurates or polyisocyanates which are deblocked during baking;

(d) a two-component system comprising (poly)ketimines and aliphatic or aromatic isocyanates, isocyanurates or polyisocyanates;

(e) a two-component system comprising (poly)ketimines and an unsaturated acrylate resin or a polyacetoacetate resin or a methacrylamidoglycolate methyl ester;

(f) a two-component system comprising carboxyl- or amino-containing polyacrylates and polyepoxides;

(g) a two-component system comprising acrylate resins containing anhydride groups and on a polyhydroxy or polyamino component;

(h) a two-component system comprising (poly)oxazolines and acrylate resins containing anhydride groups, or unsaturated acrylate resins, or aliphatic or aromatic isocyanates, isocyanurates or polyisocyanates;

(i) a two-component system comprising unsaturated polyacrylates and polymalonates;

(j) thermoplastic polyacrylate system comprising thermoplastic acrylate resins or externally crosslinking acrylate resins in combination with etherified melamine resins; and (k) a system comprising siloxane-modified or fluorine-modified acrylate resins.

Such binder-containing compositions may firer comprise a curing catalyst, or an organic solvent, and may be radiation-curable. In particular, such compositions may serve as coating compositions.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a poly-trisaryl-1,3,5-triazine carbamate compound.

Preference is additionally given to photographic materials which have a layer comprising a compound of the formula (I)–(V) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (I)–(V) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (I)–(V), which are used in accordance with the invention, can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, or alkylamides and phenols.

Preferred color couplers for use in the compositions of the invention, examples of such compounds, further additives such as color cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-0531258 and EP-A-0520938 and in the literature cited therein.

The invention also relates to a process for the stabilization of polyolefin or polyolefin copolymer films for agricultural applications, especially greenhouse applications, this polyolefin or polyolefin copolymer film having improved light stability and pesticide resistance, comprising incorporation of a sterically hindered amine and a metal oxide of hydroxide selected from oxides of zinc, aluminum, calcium and magnesium, and hydroxides of zinc, aluminum and calcium, into the polyolefin or polyolefin copolymer. A further subject of the invention is a greenhouse, characterized in that it is covered by a polyolefin or polyolefin copolymer film having improved light stability and pesticide resistance and stabilized with the novel poly-trisaryl-1,3,5-triazine carbamate compounds and a sterically hindered amine and a metal oxide or hydroxide selected from oxides of zinc, aluminum, calcium and magnesium, and hydroxides of zinc, aluminum and calcium, and a process for stabilizing a polyolefin or polyolefin copolymer greenhouse film against detrimental effects of pesticides and light, oxygen and/or heat, which process comprises incorporation of the novel poly-trisaryl-1,3,5-triazine carbamate compounds and a sterically hindered amine and a metal oxide or hydroxide selected from oxides of zinc, aluminum, calcium and magnesium, and hydroxides of zinc, aluminum and calcium, into said greenhouse film.

Further subjects of the invention are the use of a polyolefin copolymer film stabilized with the novel poly-trisaryl-1,3,5-triazine carbamate compounds and a sterically hindered amine and a metal oxide or hydroxide selected from oxides of zinc, aluminum, calcium and magnesium, and hydroxides of zinc, aluminum and calcium for agricultural applications involving pesticides, especially greenhouse applications, and the use of the novel poly-trisaryl-1,3,5-triazine carbamate compounds and a sterically hindered amine in combination with a metal oxide or hydroxide selected from oxides of zinc, aluminum, calcium and magnesium, and hydroxides of zinc, aluminum, calcium and magnesium, and hydroxides of zinc, aluminum and calcium for the stabilization of polyolefin or polyolefin copolymer films in contact with pesticides against photodegradation and damage by pesticides.

To form a film, forcing a quantity of the said melted composition through a film die, such as a flat film die or a circular blown film die, and forming a film therefrom. In the case where the composition is used to form a film therefrom, it is contemplated that the films may be unoriented, or may be subjected to a conventional operation to impart a degree of orientation on the film. Such a film may be oriented in one direction, such as in the machine direction, such as in the "machine direction" and/or the "transverse direction", or may be oriented in both directions, or "biaxially" oriented.

The present invention is also suitable for sheet applications.

The poly-trisaryl-1,3,5-triazine carbamate compounds of the formula (I)–(V) are suitable for the photochemical stabilization of undyed, dyed or printed fiber materials comprising for example, silk, leather, wool, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. Preferred textile fiber materials are those of cotton. The triazine and pyrimidine compounds of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formula (I)–(V) are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material.

The poly-trisaryl-1,3,5-triazine carbamate compounds can be applied to the fiber material in various ways and fixed on the fiber, especially in the form of aqueous dispersions or printing pastes.

The textile fiber materials finished with the novel compounds of the formula (I)–(V) possess improved protection against photochemical breakdown of the fiber and yellowing phenomena and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with an poly-trisaryl-1,3,5-triazine carbamate compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formulas (I)–(V) are permeable to UV radiation. The determination of the sun protection factor of textile fiber materials is explained, for example, in WO94/04515 or in J. Soc. Cosmet. Chem. 40, 127–133 (1989) and can be carried out analogously thereto.

Yet another use of the UV absorbers according to the invention is in the stabilization of intra-ocular and contact lenses.

The inventive UV absorbers are suitable as photoprotective agents in cosmetic preparations. The invention additionally relates, therefore, to a cosmetic preparation comprising at least one poly-trisaryl-1,3,5-triazine carbamate compound and cosmetically acceptable carriers or auxiliaries.

The novel cosmetic composition contains from 0.1 to 15% by weight, preferably from 0.5 to 10% by weight, based on the overall weight of the composition, of a poly-trisaryl-1,3,5-triazine carbamate UV absorber and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase can comprise any oil which is suitable for cosmetic formulations, e.g., one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For these cosmetic formulations, it is possible to use any conventionally employed emulsifier, e.g., one or more ethoxylated esters of naturally occurring derivatives, i.e., polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Example 1

Compound XIII

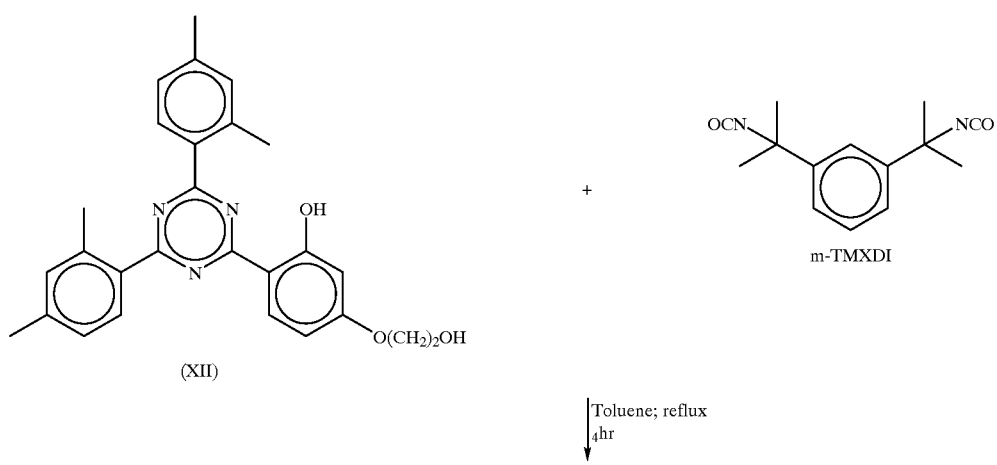

-continued

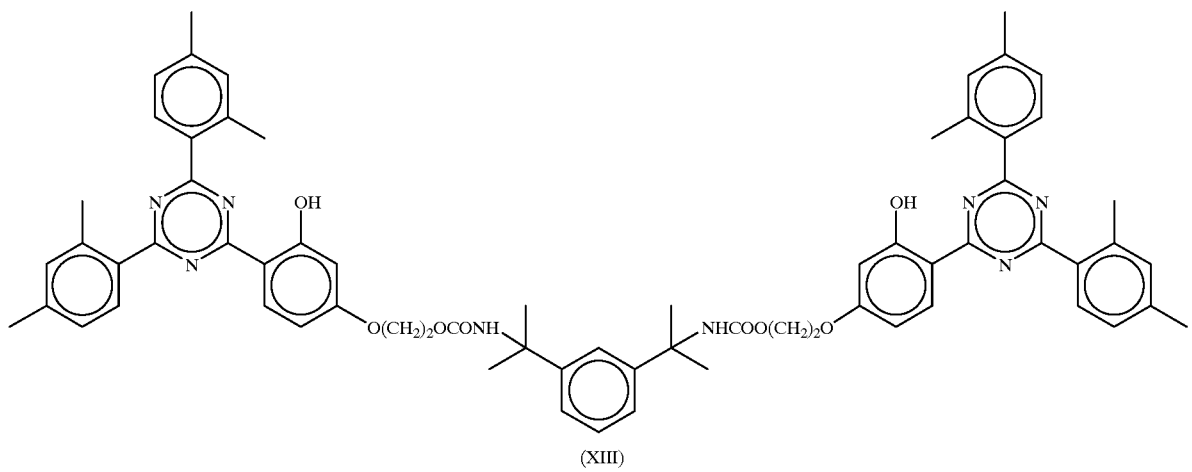

(XIII)

A mixture of 8.82 grams of (2,4-Bis(2,4-dimethylphenyl)-6-[2-hydroxy-4-(2-hydroxyethoxy)phenyl]-1,3-5-triazine), 2.43 grams of m-TMXDI® (Cytec Industries, Inc., West Paterson, N.J.) and 120 mg of 1,3-diacetoxy-1,1,3,3-tetrabutyldistannoxane ("TK-1") catalyst was heated in 50 mL of xylenes at about 120° C. for 4 hours. The TLC at this stage showed the absence of starting material and the formation of a major product. The heating was discontinued and the mixture allowed to cool to room temperature. It was then concentrated under reduced pressure to give 11.5 grams of crude XIII. An analytical sample was prepared by purifying the crude product using column chromatography over silica gel. The structure of the product was confirmed to be XIII based on NMR and mass spectra.

Example 2

Compound XV

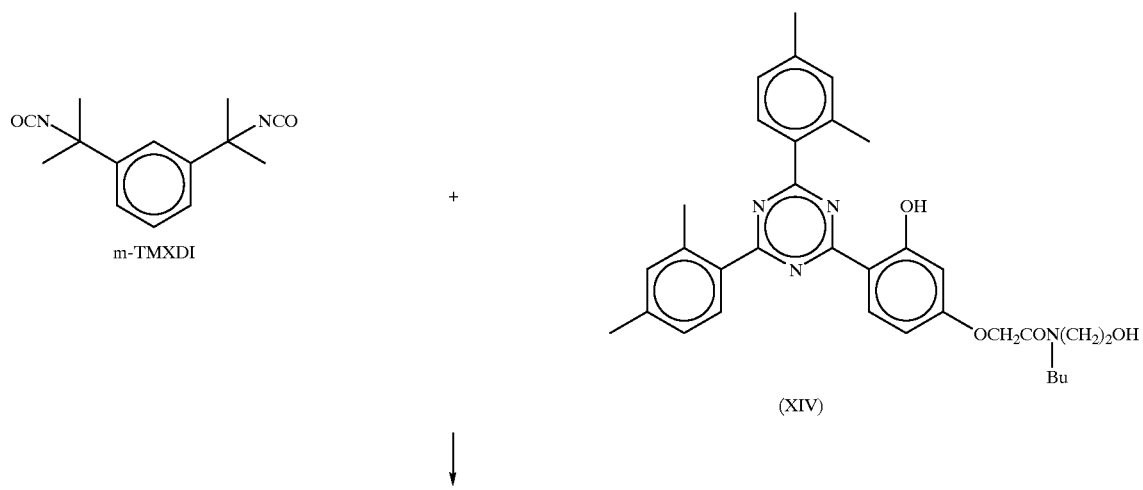

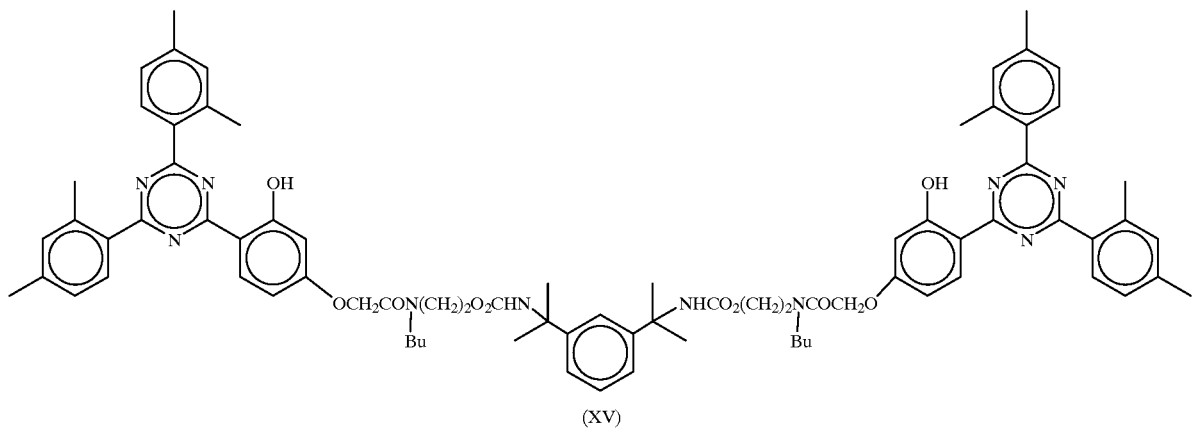
(XV)
Following example 1, m-TMXDI is reacted with 2-(2-hydroxy4-(N-(n-butyl)-N-(2-hydroxyethyl)-metharnmidooxy)phenyl)-4,6-bis(2,4-dimethylphenyl)-1,3,5-triazine (Compound XIV) in the presence of TK-1 as a catalyst in xylenes to form compound XV.
Example 3
Compound XVI
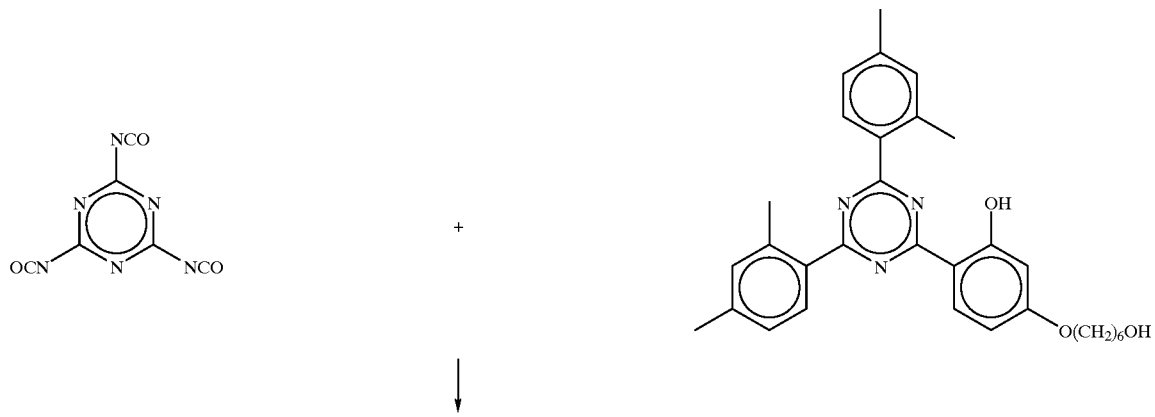

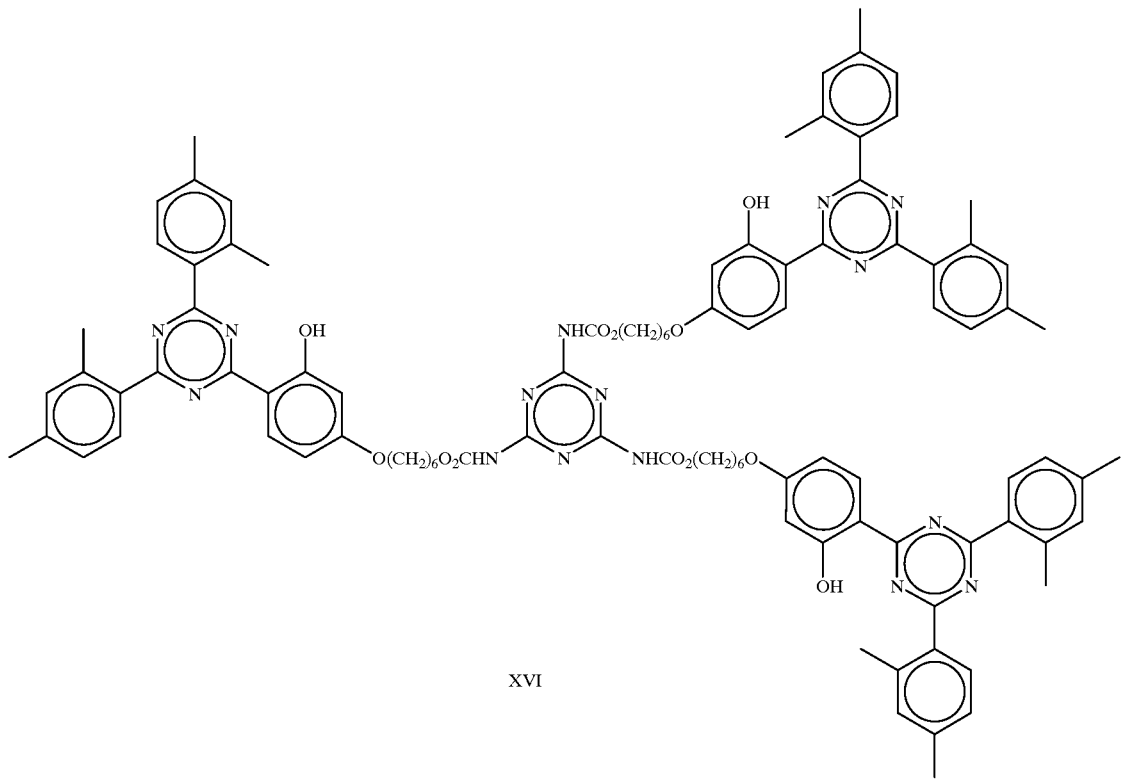

XVI

A mixture of 2.04 g of 2,4,6-trisisocyanato-1,3,5-triazine (melamine triisocyanate), 14.9 g of 2,4-bis(2,4-dimethylphenyl)-6-{2-hydroxy-4-(2-hydroxyhexyloxy)phenyl}-1,3,5-triazine and 200 mg of TK-1 is heated to 120° C. in 100 mL of xylenes for 4 hr. The reaction mixture is allowed to cool to room temperature and solvent removed under reduced pressure to give compound XVI which can be purified by column chromatography over silica gel.

Example 4

Compounds XVI, XVII and XVIII

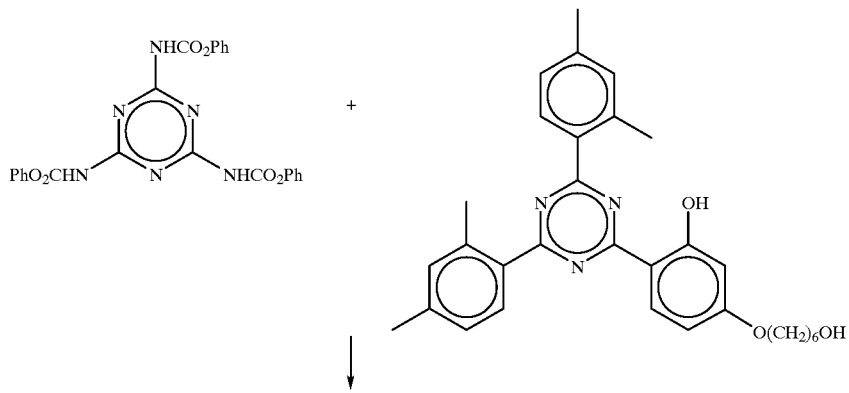

-continued

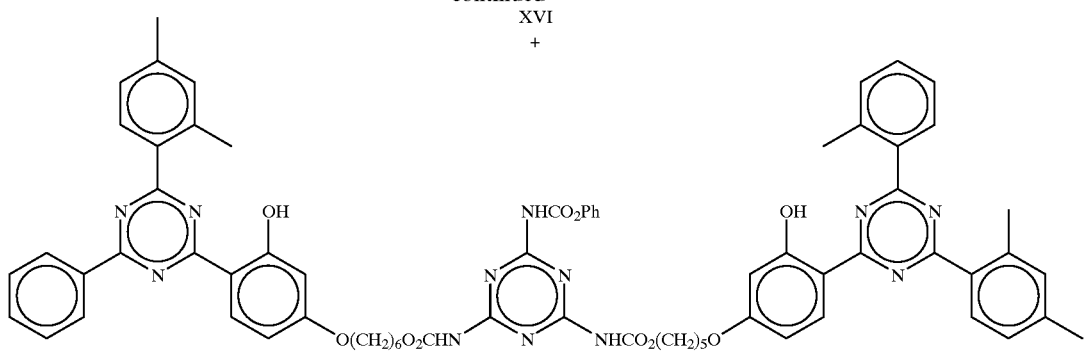

XVI
+

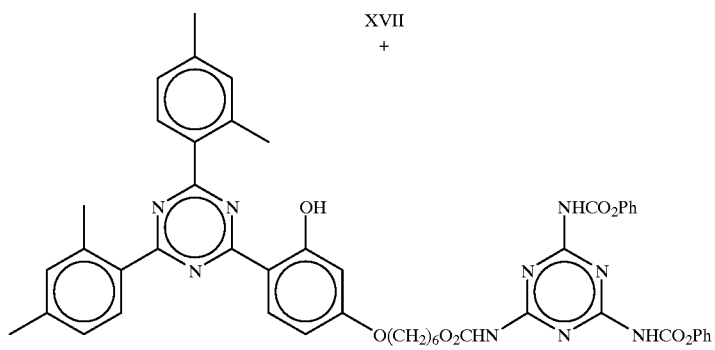

XVIII

A mixture of 0,972 g of 2,4,6-trisphenylcarbamoyl-1,3,5-triazine, 2.98 g of 2,4-bis(2,4-dimethylphenyl)-6-{2-hydroxy-4-(2-hydroxyhexyloxy)phenyl}-1,3,5-triazine and 100 mg of TK-1 is heated to 120° C. in xylenes for 6 hr. The reaction mixture is analyzed for the disappearance of 2,4,6-trisphenylcarbamoyl-1,3,5-triazine. The formation of new products XVI, XVII and XVIII is indicated by TLC (thin layer chromatography).

Example 5
Isothermal Thermogravimetric Analysis of XIII

Duplicate specimens of XIII and Tinuvin 1577 were heated in a Perkin-Elmer 7 Series thermobalance from 20–320° C. at 40° C./min and held isothermally at 320° C. for 60 min. Air was used as the purge gas (flow rate of ~25 mL/min). The temperature of 320° C. is one that is used during injection molding of certain engineered thermoplastics, for example polycarbonate. As can be seen from Table I, XIII is significantly less volatile at 320° C. than Tinuvin 1577, a current art triazine stabilizer.

TABLE I

CUMULATIVE PERCENT WEIGHT LOSS OF STABILIZERS AT 320° C.

| | | Time at 320° C. (min.) | | | |
|---|---|---|---|---|---|
| Stabilizer | a | 30 | 45 | 60 | Total |
| XIII | 0.4 | 41.5 | 49.5 | 53.3 | 54.1 |
| Tinuvin 1577 | 0.1 | 50.7 | 73.3 | 85.3 | 86.1 | a) Percent loss while heating from 20° C. to 320° C.

Example 6
Initial Color of Stabilized Polycarbonate Compositions

Polycarbonate plaques were prepared as follows. GE Lexan 105 barefoot natural flake polycarbonate resin (melt temperature 310–333° C.) was dry blended with 0.35% stabilizer plus 0.10 wt % Mark® 2112 phosphite. The blended compositions were melt-mixed and extruded in a Haake torque rheometer equipped with a a 0.75-inch 25:1 single mixing screw extruder. The zone temperatures were 246, 265, 295, and 304° C. The extruded polycarbonate was pulled through a water bath, dried, pelletized, and redried at 120° C. for 4–48 hr in a forced air oven. The pellets were injection molded at 305–310° C. using an Arburg "Allrounder" hydraulic injection molder to form 2×2.5×0.100-inch plaques. The mold temperature was 100° C. Yellow indices and delta E data were obtained using a Macbeth Color Eye Colorimeter with illuminate C, 2° observer, specular component excluded, and UV component included. As can be seen from Table 2, XIII affords lower initial color than Compound A (2-(2-hydroxy-4ethoxycarbonylmethoxyphenyl-4,6-bis(2,4-dimethylphenyl)-1,3,5-triazine) and Compound B (2-(2-hydroxy-4-(2-ethylhexanoyl))-4,6-bis(2,4-dimethylphenyl)-1,3,5-triazine), current art triazine UV stabilizers.

TABLE 2

YELLOW INDICES OF POLYCARBONATE COMPOSITIONS

| Stabilizer | Yellow Index[a] |
|---|---|
| XIII | 14.7 |
| A | 18.0 |
| B | 18.2 |

[a]Average value from two plaques.

Example 7
Xenon Arc Weathering of Polycarbonate Composition Containing XIII Stabilized polycarbonate plaques were prepared as described in Example 5. The plaques were subjected to 400 hr. of xenon arc weathering following ASTM G-26 using Test Method B with alternate exposure to light and darkness and an intermittent exposure to water spray maintaining an atmosphere temperature of 63°±3°C. and a relative humidity of 30°±5% (Miami, Fla. conditions). Irradiance was 0.35 W/m² at 340 nm. The results are summarized in Table 3.

TABLE 3

XENON ARC WEATHERING (400 hr.) OF STABILIZED POLYCARBONATE COMPOSITIONS

| Stabilizer | Yellow Index |
|---|---|
| None | 5.3 |
| XIII | 2.8 |
| A | 3.8 |
| B | 3.7 |

Example 8
QUV Weathering of Clear Coating Compositions Containing Carbamate Triazine Dimer XIII The appropriate UV absorber and/or Sanduvor 3055 (1% based on total resin solids) were pre-dissolved in the solvent mixture (5–10% solids) and added to the clear acrylic urethane formulation given in Table 4. Components I and II of were mixed just before use. Cold roll steel panels measuring 4"×12" and pre-coated with ED5050A E-coat and #542AB839 white base-coat, obtained from ACT Laboratories, Inc. (Hillsdale, Mich.) were used. The drawdown technique, using WC-60 Wire-Cators™ (Leneta Co., Ho-Ho-Kus, N.J.) was used to apply the clear coat compositions to the pre-coated panels. The clear coats were allowed to flash for 10 min at ambient temperature and cured for 30 min at 135° C.

TABLE 4

Acrylic Urethane Clear Coat Formulation

| Raw Material | Supplier | Amount |
|---|---|---|
| Component I | | |
| Joncryl ® CDX-588 Acrylic Resin (70% Solids) | S.C. Johnson & Son, Inc. Racine, Wisconsin | 100 parts |
| T-12 (2% Solids in Catalyst Solution) | | 5 parts |
| Solvent Mixture | | 45 parts |
| UV Absorber | | 2 parts[a] |
| Sanduvor ® S-3055 | Clariant Corporation, Charlotte, N.C. | 1 part[b] |
| Component II | | |
| Desmodur ® N-3390 (90% Solids) | Miles Inc., Pittsburgh, Pennsylvania | 33 parts |
| Solvent Mixture | | 17 parts |
| Catalyst Solution | | |
| T-12 (Dibutyltin dilaurate) | Air Products | 1 part |
| Acetic Acid | | 4 parts |
| PM Acetate | | 45 parts |
| Solvent Mixture: | | |
| Xylenes | | 1 part |
| PM Acetate | | 1 part |
| MAK | | 1 part |

[a]Amount for 2% based on total resin solids
[b]Amount for 1% based on total resin solids Accelerated weathering was carried out on the coatings with a QUV device equipped with UVB-313 fluorescent bulbs. Specular properties (gloss and distinctness of image, or DOI) and yellowing (delta b) were measured as a function of weathering time. The effects of carbamate triazine dimer XIII alone, and in combination with S3055, on weatherability are given in Tables 5–7. Compositions containing XIII have longer times to failure than the unstabilized control. The effect of XIII alone on yellowing under QUV exposure is given in Table 5. The yellowing of the stabilized compositions was less than the unstabilized control, and also less than compositions containing Compound C, a prior art triazine UV absorber. Furthermore, the data show that the XIII/S-3055 combination has a synergistic effect on yellowing as well as time to failure.

TABLE 5

QUV Weathering (UVB-313 Bulbs) of a 2 k Acrylic Urethane Clear Coat Compositions Containing XIII, Effect on Yellowing (Delta b)

| | Hours QUV Exposure | | | | |
|---|---|---|---|---|---|
| Stabilizer | 2499 | 3003 | 3504 | 4978 | 5500 |
| None | 8.05 | 9.14 | 8.86[a] | — | — |
| 2% XIII | 5.70 | 5.17 | 5.84 | 5.69 | 5.74 |
| 2% C | 5.45 | 5.63 | 6.46 | 6.50 | 5.96 |

TABLE 5-continued

QUV Weathering (UVB-313 Bulbs) of a 2 k Acrylic Urethane Clear Coat Compositions Containing XIII, Effect on Yellowing (Delta b)

| | Hours QUV Exposure | | | | |
|---|---|---|---|---|---|
| Stabilizer | 2499 | 3003 | 3504 | 4978 | 5500 |
| 1% XIII, 1% S-3055 | 3.00 | 3.33 | 3.89 | 3.94 | 4.21 |
| 2% S-3055 | 4.57 | 5.91 | 7.82 | 8.46[a] | — |

[a]Coating failed.
[b]C is a mixture of 2-[4-((2-hydroxy-3-dodecyloxypropyl)-oxy)-2-hydroxyphenyl]-4,6-bis(2,4-dimethylphenyl)-1,3,5-triazine and 2-[4-((2-hydroxy-3-tridecyloxypropyl)-oxy)-2-hydroxyphenyl]-4,6-bis(2,4-dimethylphenyl)-1,3,5-triazine The effects of carbamate triazine dimer XIII on gloss retention and DOI retention under QUV exposure are given in Tables 6 and 7. The compositions containing XIII showed improved gloss and DOI retention compared to the control, and also compared to compositions containing XIV, a prior art triazine UV absorber. Furthermore, the data show that the XIII/S-3055 combination has a synergistic effect on both gloss and DOI retention.

TABLE 6

QUV Weathering (UVB-313 Bulbs) of a 2 k Acrylic Urethane Clear Coat Compositions Containing XIII, Effect on Percent Gloss Retention

| | Hours QUV Exposure | | | | | | |
|---|---|---|---|---|---|---|---|
| Stabilizer | 2499 | 3003 | 3504 | 3988 | 4484 | 4978 | 5500 |
| None | 57.0 | 10.2 | a | — | — | — | — |
| 2% XIII | 100.7 | 85.2 | 70.1 | 51.7 | 44.5 | 39.3 | 44.7 |
| 2% C | 99.0 | 80.8 | 64.3 | 46.5 | 28.1 | 27.1 | 14.3 |
| 1% XIII, 1% S-3055 | 103.6 | 91.5 | 95.1 | 83.2 | 66.8 | 65.8 | 50.1 |
| 2% S-3055 | 105.2 | 98.5 | 97.2 | 91.2 | 59.7 | a | — | a) Coating failed.
b) C is a mixture of 2-[4-((2-hydroxy-3-dodecyloxypropyl)-oxy)-2-hydroxyphenyl]-4,6-bis(2,4-dimethylphenyl)-1,3,5-triazine and 2-[4-((2-hydroxy-3-tridecyloxypropyl)-oxy)-2-hydroxyphenyl]-4,6-bis(2,4-dimethylphenyl)-1,3,5-triazine

TABLE 7

QUV Weathering (UVB-313 Bulbs) of 2 k Acrylic Urethane Clear Coat Compositions Containing XIII, Effect on Percent DOI Retention

| | Hours QUV Exposure | | | | | | |
|---|---|---|---|---|---|---|---|
| Stabilizer | 2499 | 3003 | 3504 | 3988 | 4484 | 4978 | 5500 |
| None | 44.0 | 0.9 | 0.0[a] | — | — | — | — |
| 2% XIII | 98.3 | 80.2 | 74.8 | 47.6 | 54.2 | 46.6 | 45.2 |
| 2% C | 98.1 | 81.5 | 68.3 | 36.5 | 29.8 | 29.8 | a |
| 1% XIII, 1% S-3055 | 101.1 | 101.2 | 100.5 | 84.0 | 57.5 | 71.2 | 55.4 |
| 2% S-3055 | 100.5 | 101.5 | 96.8 | 76.8 | 23.2 | a | — | a) Coating failed.
b) C is a mixture of 2-[4-((2-hydroxy-3-dodecyloxypropyl)-oxy)-2-hydroxyphenyl]-4,6-bis(2,4-dimethylphenyl)-1,3,5-triazine and 2-[4-((2-hydroxy-3-tridecyloxypropyl)-oxy)-2-hydroxyphenyl]-4,6-bis(2,4-dimethylphenyl)-1,3,5-triazine

Example 9
Xenon Arc Weathering of Clear Coating Compositions Containing Carbamate Triazine Dimer XIII Accelerated weathering was carried out on the clear coat compositions of Example 7 with an Atlas Ci65 WeatherOmeter equipped with xenon arc lamps and following the SAE J1960 automotive exterior test protocol. Specular properties (gloss and distinctness of image, or DOI) and yellowing (delta b) were measured as a function of weathering time. The effect of carbamate triazine dimer XIII on weatherability are given in Tables 8–10. The composition containing XIII has a longer time to failure than the unstabilized control (>9000 hr. vs 8000 hr.). The effect of XIII on yellowing under xenon are exposure is given in Table 8. The yellowing of the stabilized composition was less than the unstabilized control, especially at 8000 hr.

TABLE 8

Xenon Arc Weathering (SAE J1960 Automotive Exterior) of 2 k Acrylic Urethane Clear Coat Compositions Containing XIII, Effects on Yellowing (Delta b)

| | Hours Xenon Exposure | | | | | | | |
|---|---|---|---|---|---|---|---|---|
| Stabilizer | 3002 | 4014 | 5500 | 6000 | 6500 | 7500 | 8000 | 9000 |
| None | 2.04 | 2.33 | 2.93 | 2.99 | 3.24 | 3.33 | 8.13[a] | — |
| 2% XIII | 1.78 | 1.80 | 1.96 | 2.11 | 2.38 | 2.32 | 2.21 | 2.64 |

[a]Coating failed.

The effects of carbamate triazine dimer XIII on gloss retention and DOI retention under xenon arc exposure are given in Tables 9 and 10. Gloss and DOI loss for the composition XIII is much less than that for the unstabilized coating, which fails at 8000 hr. DOI proved to be a more sensitive measure of degradation in this case. The composition containing XIII began to distinguish itself from the control within 3000 hr, so this earlier data is listed.

TABLE 9

Xenon Arc Weathering (SAE J1960 Automotive Exterior) of 2 k Acrylic Urethane Clear Coat Compositions Containing XIII, Effect on Percent Gloss Retention

| | Hours Xenon Exposure | | | | | |
|---|---|---|---|---|---|---|
| Stabilizer | 5500 | 6000 | 6500 | 7500 | 8000 | 9000 |
| None | 80.9 | 68.7 | 60.8 | 39.0 | 6.8[a] | — |
| 2% XIII | 90.1 | 81.1 | 85.5 | 74.7 | 41.8 | 34.8 |

[a]Coating failed.

TABLE 10

Xenon Weathering (SAE J1960 Automotive Exterior) of 2 k Polyurethane Acrylic Coating Compositions Containing XIII, Effect on Percent DOI Retention

| | Hours Xenon Exposure | | | | | | | |
|---|---|---|---|---|---|---|---|---|
| Stabilizer | 3002 | 4014 | 5500 | 6000 | 6500 | 7500 | 8000 | 9000 |
| None | 92.5 | 83.2 | 73.7 | 58.1 | 52.4 | 37.1 | 0.8[a] | — |
| 2% XIII | 106.6 | 103.8 | 103.6 | 98.2 | 97.9 | 96.1 | 52.2 | 35.8 |

[a]Coating failed.

What is claimed is:

1. A compound selected from the group consisting of compounds of formula (I), (II) and (III):

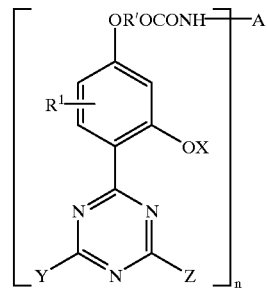
(I)

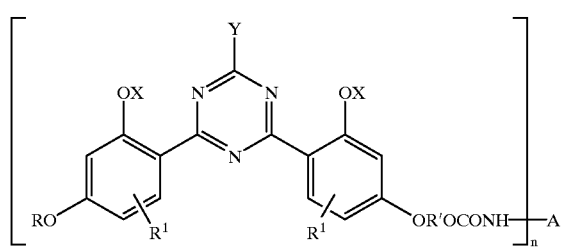
(II)

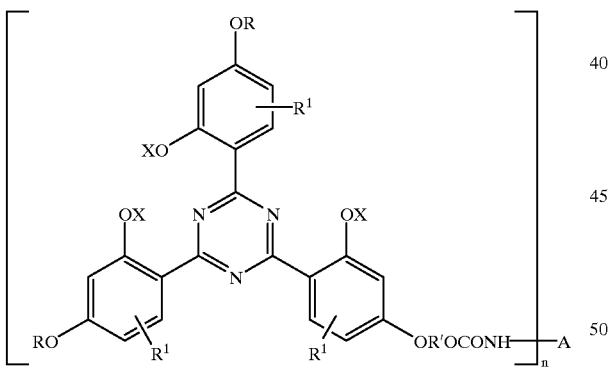
(III)

wherein:

(a) A is a polyvalent hydrocarbyl or a polyvalent 1,3,5-triazine;

(b) each X is independently hydrogen, allyl, —$COR^a$, —$SO_2R^b$, $SiR^cR^dR^e$, —$PR^fR^g$, or —$POR^fR^g$;

(c) each of Y and Z is independently an aryl ring of formula (IV):

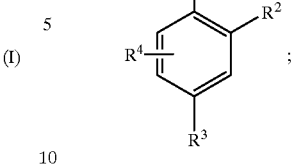
(IV)

(d) each R is independently a hydrocarbyl group or a functional hydrocarbyl group; and is different from each other R group; each R' is independently a hydrocarbylene group, a functional hydrocarbylene group or the group —$CH_2CONC_4H_9(CH_2)_2$—;

(e) each $R^a$ is independently $C_1$–$C_8$ alkyl, halogen-substituted $C_1$–$C_8$ alkyl, $C_5$–$C_{12}$ cycloalkyl, $C_2$–$C_8$ alkenyl, —$CH_2$—$CO$—$CH_3$, $C_7$–$C_{12}$ aralkyl, $C_1$–$C_{12}$ alkoxy, or phenyl which is unsubstituted or substituted by $C_1$–$C_{12}$ alkyl, $C_1$–$C_4$ alkoxy, halogen and/or benzyl;

(f) each $R^b$ is independently $C_1$–$C_{12}$ alkyl, $C_6$–$C_{10}$ aryl, or $C_7$–$C_{18}$ alkylaryl;

(g) each $R^c$, $R^d$, and $R^e$ is independently $C_1$–$C_{18}$ alkyl, cyclohexyl, phenyl, or $C_1$–$C_{18}$ alkoxy;

(h) each $R^f$ and $R^g$ is independently $C_1$–$C_{12}$ alkoxy, phenoxy, $C_1$–$C_{12}$ alkyl, $C_5$–$C_{12}$ cycloalkyl, benzyl, tolyl, or phenyl;

(i) each $R^1$, $R^2$ and $R^4$ is independently hydrogen, hydrocarbyl, functional hydrocarbyl, —O(hydrocarbyl), —O(functional hydrocarbyl), —SR, halogen, —$SO_3R$, —COOR, —COR, —OCOR, —NRR or cyano;

(j) each $R^3$ is independently R, —OR, —SR, halogen, —$SO_3R$, —COOR, —COR, —NRR or cyano; and (k) n is an integer between 2 and about 50.

2. A compound according to claim 1, selected from the group consisting of compounds of formula (V), (VI) or (VII):

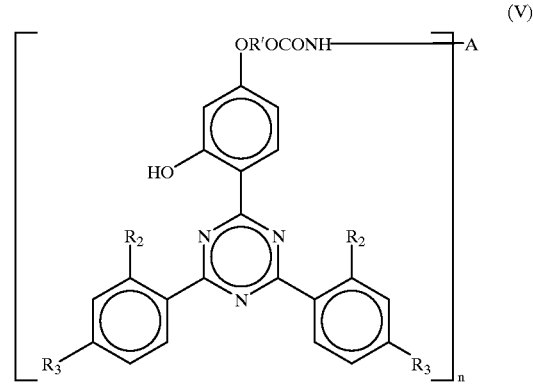
(V)

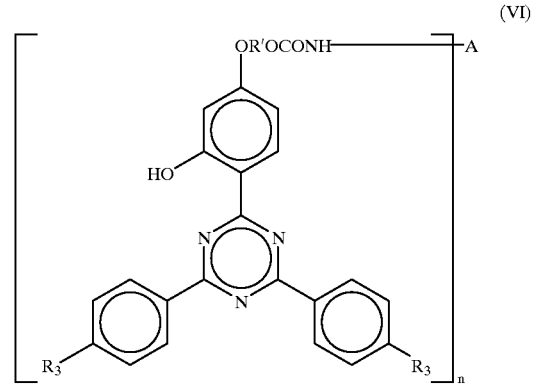
(VI)

(VII)

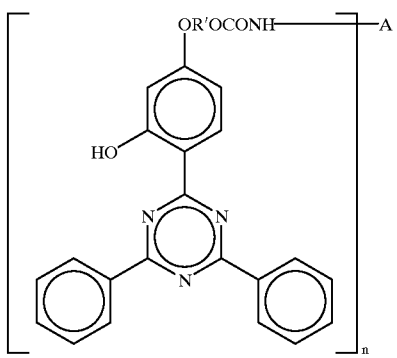

wherein:

(a) A is a polyvalent hydrocarbyl or a heterocyclic ring;
(b) each R is independently selected from a hydrocarbyl group and a functional hydrocarbyl group; and is different from each other R group;
(c) each $R^2$ is independently selected from hydrogen, a hydrocarbyl group of 1 to 24 carbon atoms, a hydrocarbyloxy group of 1 to 24 carbon atoms, and an acyloxy group of 1 to 24 carbon atoms;
(d) each $R^3$ is independently selected from hydrogen, a hydrocarbyl group of 1 to 24 carbon atoms, a functional hydrocarbyl group of 1 to 24 carbon atoms and —OR; and
(e) n is 2 or 3.

3. A compound according to claim 1, selected from the group consisting of compounds of formula (VIII), (IX) or (X):

(VIII)

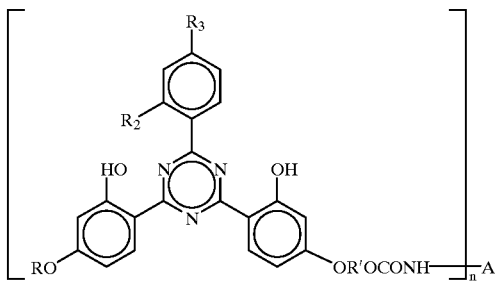

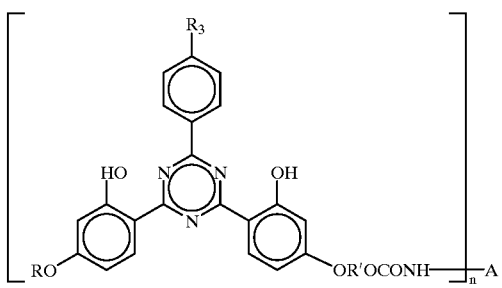

(X)

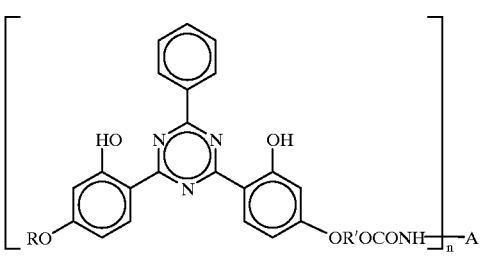

wherein:

(a) A is a polyvalent hydrocarbyl or a heterocyclic ring;
(b) each R is independently selected from a hydrocarbyl group and a functional hydrocarbyl group; and is different from each other R group;
(c) $R^2$ is selected from hydrogen, a hydrocarbyl group of 1 to 24 carbon atoms, a hydrocarbyloxy group of 1 to 24 carbon atoms, and an acyloxy group of 1 to 24 carbon atoms;
(d) $R^3$ is selected from hydrogen, a hydrocarbyl group of 1 to 24 carbon atoms, a functional hydrocarbyl group of 1 to 24 carbon atoms and —OR; and
(e) n is 2 or 3.

4. The compound of claims 2 or 3, wherein each $R^2$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain, and an acyloxy of 2 to 12 carbon atoms and A is selected from the group consisting of:

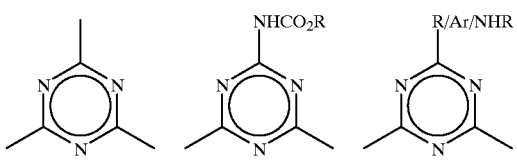

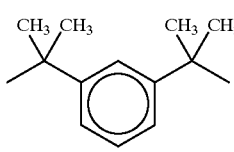

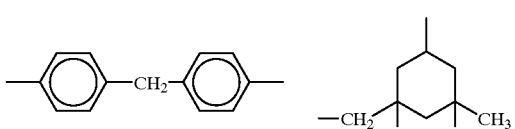

-continued

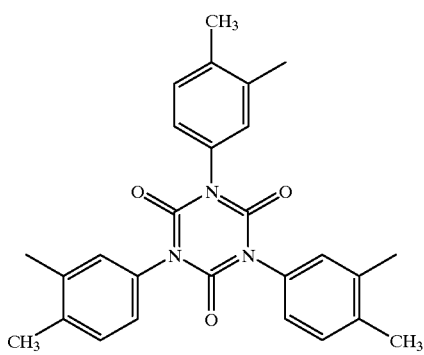

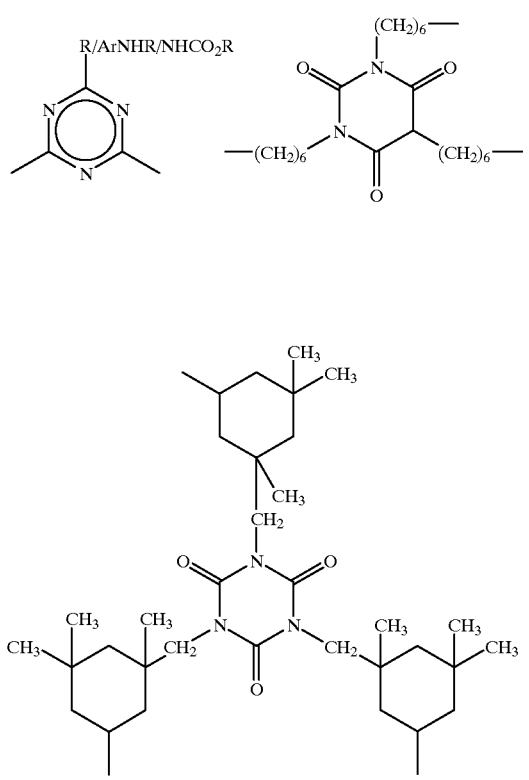

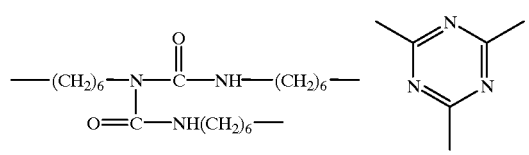

-continued

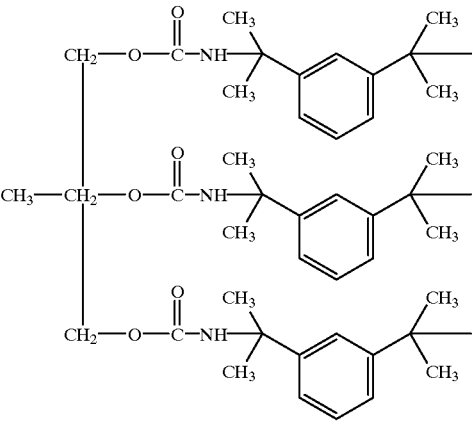

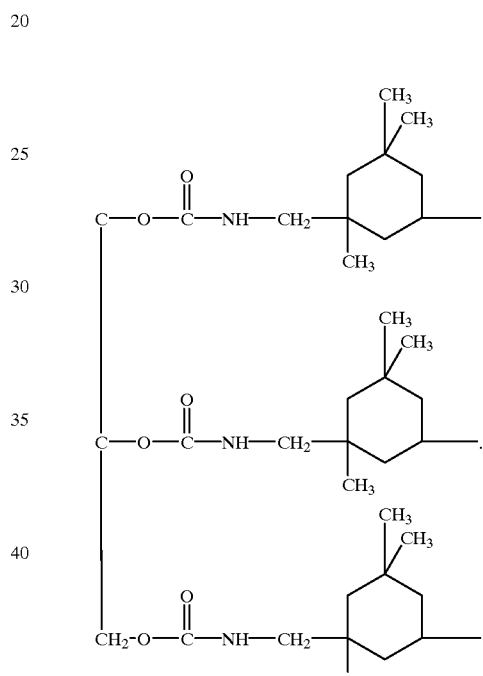

5. A composition comprising at least one compound of claim 1.

6. The compound of claim 4, wherein each $R^2$ is independently selected from hydrogen, R, —OR and an alkyl of 1 to 4 carbon atoms and A is selected from the group consisting of polyisocyanate residues formed by the reaction of two or more trisaryl-1,3,5-triazine compounds, each having at least one aryl ring with a hydroxyl group para to the point of attachment to the triazine ring, and being further substituted by a hydroxyl functional hydrocarbyl group, with a polyvalent hydrocarbyl compound such as a diisocyanate, a triisocyanate or a polyisocyanate.

7. The compound of claim 6, wherein each $R^2$ is independently selected from hydrogen, $C_1$–$C_4$ alkoxy and methyl and A is selected from the group consisting of polyisocyanate residues formed by the reaction of two or more trisaryl-1,3,5-triazine compounds, each having at least one aryl ring with a hydroxyl group para to the point of attachment to the triazine ring, and being further substituted by a hydroxyl functional hydrocarbyl group, with a polyvalent hydrocarbyl compound such as a diisocyanate, a triisocyanate or a polyisocyanate.

8. The compound of claims 2 or 3, wherein each $R^3$ is independently selected from hydrogen, an alkyl of 1 to 24 carbon atoms optionally containing an oxygen atom in the chain, a hydroxyalkyl of 1 to 24 carbon atoms group optionally containing an oxygen atom in the chain, R and —OR.

9. The compound of claim 8, wherein each $R^3$ is independently selected from hydrogen, an alkyl of 1 to 4 carbon atoms and —OR.

10. The compound of claim 9, wherein each $R^3$ is independently selected from hydrogen, methyl, $C_1$–$C_4$ alkoxy and tertiary butyl.

11. A method of stabilizing a material which is subject to degradation by actinic radiation which comprises the addition to said material of an effective amount of at least one compound selected from the group consisting of compounds of formula (I), (II) and (III)

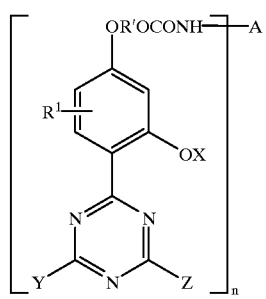
(I)

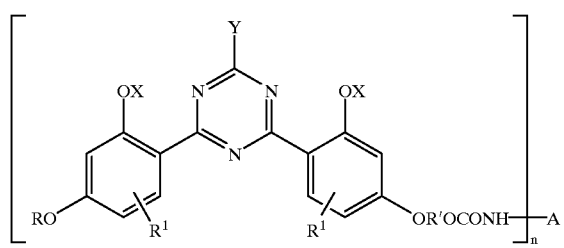
(II)

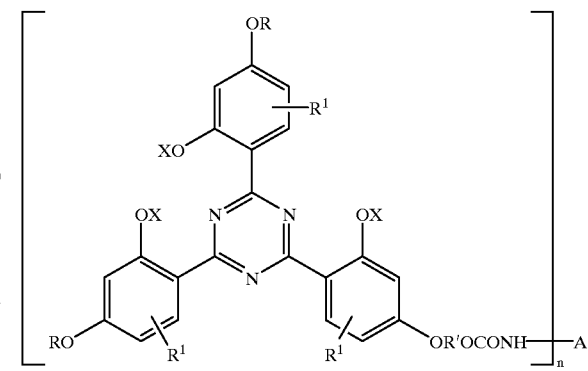
(III)

wherein:

(a) A is a polyvalent hydrocarbyl or a polyvalent 1,3,5-triazine;

(b) each X is independently hydrogen, allyl, —$COR^a$, —$SO_2R^b$, $SiR^cR^dR^e$, —$PR^fR^g$, or —$POR^fR^g$;

(c) each of Y and Z is independently an aryl ring of formula (IV)

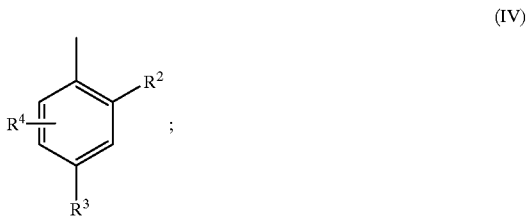
(IV)

(d) each R is independently a hydrocarbyl group or a functional hydrocarbyl group; and is different from each other R group; each R' is independently a hydrocarbylene group, a functional hydrocarbylene group or the group —$CH_2CONC_4H_9(CH_2)_2$—;

(e) each $R^a$ is independently $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_7$–$C_{12}$ aralkyl, $C_1$–$C_{12}$ alkoxy, or phenyl which is unsubstituted or substituted by $C_1$–$C_{12}$ alkyl, $C_1$–$C_4$ alkoxy, halogen and/or benzyl;

(f) each $R^b$ is independently $C_1$–$C_{12}$ alkyl, $C_6$–$C_{10}$ aryl, or $C_7$–$C_{18}$ alkylaryl;

(g) each $R^c$, $R^d$, and $R^e$ is independently $C_1$–$C_{18}$ alkyl, cyclohexyl, phenyl, or $C_1$–$C_{18}$ alkoxy;

(h) each $R^f$ and $R^g$ is independently $C_1$–$C_{12}$ alkoxy, phenoxy, $C_1$–$C_{12}$ alkyl, $C_5$–$C_{12}$ cycloalkyl, benzyl, tolyl, or phenyl;

(i) each $R^1$, $R^2$ and $R^4$ is independently hydrogen, hydrocarbyl, functional hydrocarbyl, —O(hydrocarbyl), —O(functional hydrocarbyl), —SR, halogen, —SO₃R, —COOR, —COR, —OCOR, —NRR or cyano;

(j) each $R^3$ is independently R, —OR, —SR, halogen, —SO₃R, —COOR, —COR, —NRR or cyano; and (k) n is an integer between 2 and about 50.

12. The method of claim 11, wherein the compound of formula (I), (II) or (III) is added in an amount from about 0.01 to about 20% by weight based on the weight of the material to be stabilized.

13. The method of claim 11, wherein the compound of formula (I), (II) or (III) is added in an amount from about 0.1 to about 10% by weight based on the weight of the material to be stabilized.

14. The method of claim 13, wherein said material to be stabilized is a polymer.

15. The method of claim 14, wherein said polymer is a thermoplastic polymer.

16. The method of claim 15, wherein said thermoplastic polymer is a polycarbonate.

17. The method of claim 15, wherein said thermoplastic polymer is a polyketone.

18. The method of claim 15, wherein said thermoplastic polymer is a polyamide or polyamide blend.

19. The method of claim 15, wherein said thermoplastic polymer is a polyolefin.

20. The method of claim 15, wherein said thermoplastic polymer is a polyurethane or polyurethane blend.

21. The method of claim 11, which further comprises incorporating into said material at least one additional additive, said additive selected from the group consisting of: antioxidants, ultraviolet light absorbers, ultraviolet light stabilizers, metal deactivators, phosphites, phosphonites, hydroxylamines, nitrones, thiosynergists, peroxide scavengers, polyamide stabilizers, nucleating agents, fillers, reinforcing agents, plasticizers, lubricants, emulsifiers, pigments, rheological additives, flameproofing agents, antistatic agents, blowing agents, benzofuranones and indolinones.

22. The method of claim 21, wherein said additional additive is a sterically hindered amine or a UV absorber.

23. The method of claim 21, wherein said additional additive is a benzotriazole, benzophenone, oxamide, acrylate or other triazine.

24. The method of claim 22, wherein said sterically hindered amine comprises at least one member of the group consisting of: bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; N-(2,2,6,6-tetramethylpiperidin-4-yl)-n-dodecylsuccinimide; N-(1,2,2,6,6-pentamethylpiperidin-4-yl)-n-dodecylsuccinimide; 2-undecyl-7,7,9,9-tetramethyl-1-oxa-3,8-diaza-4-oxospiro[4.5]decane; the reaction product of 7,7,9,9-tetramethyl-2-cycloundecyl-1-oxa-3,8-diaza-4-oxospiro[4.5]decane and epichlorohydrin; and derivatives thereof.

25. The method of claim 14, which further comprises forming a shaped article from said polymer.

26. The method of claim 11 which further comprises applying the material, to which an effective amount of a compound of formula (I), (II) or (III) has been added, to the outer surface of a substrate.

27. The method of claim 26, wherein the material is a polymer.

28. The method of claim 27, wherein said stabilized polymer is applied to said substrate in the form of a film.

29. The method of claim 28, wherein said substrate comprises a metallic, wood, ceramic or polymeric material.

30. The method of claim 28, wherein said substrate comprises more than one layer.

31. The method of claim 11, wherein said material comprises a fiber material.

32. The method of claim 31, wherein said fiber material is selected from the group consisting of silk, leather, wool, polyamide, polyurethane, cellulose-containing fiber and blends thereof.

33. The method of claim 11, wherein said material comprises a cosmetic composition.

34. An actinic radiation stabilizing composition which comprises a binder and a compound selected from the group consisting of compounds of formula (I), (II) and (III):

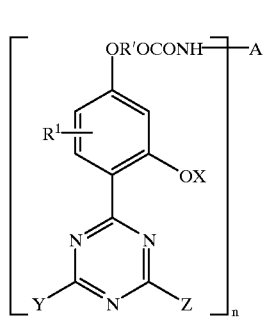

(I)

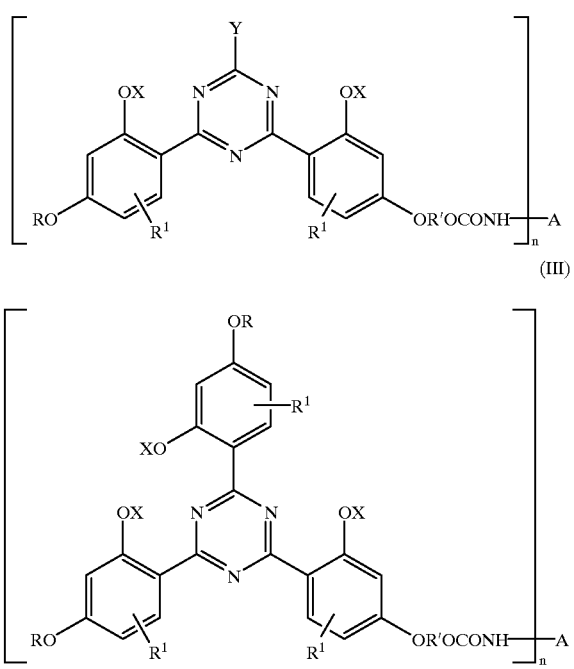

wherein:
(a) A is a polyvalent hydrocarbyl or a polyvalent 1,3,5-triazine;
(b) each X is independently hydrogen, allyl, —COR$^a$, —SO$_2$R$^b$, SiR$^c$R$^d$R$^e$, —PR$^f$R$^g$, or —POR$^f$R$^g$;
(c) each of Y and Z is independently an aryl ring of formula (IV)

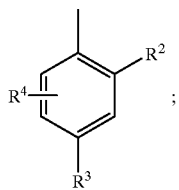

(d) each R is independently a hydrocarbyl group or a functional hydrocarbyl group; and is different from each other R group; each R' is independently a hydrocarbylene group, a functional hydrocarbylene group or the group —CH$_2$CONC$_4$H$_9$(CH$_2$)$_2$—;
(e) each R$^a$ is independently C$_1$–C$_8$ alkyl, halogen-substituted C$_1$–C$_8$ alkyl, C$_5$–C$_{12}$ cycloalkyl, C$_2$–C$_8$ alkenyl, —CH$_2$—CO—CH$_3$, C$_7$–C$_{12}$ aralkyl, C$_1$–C$_{12}$ alkoxy, or phenyl which is unsubstituted or substituted by C$_1$–C$_{12}$ alkyl, C$_1$–C$_4$ alkoxy, halogen and/or benzyl;
(f) each R$^b$ is independently C$_1$–C$_{12}$ alkyl, C$_6$–C$_{10}$ aryl, or C$_7$–C$_{18}$ alkylaryl;
(g) each R$^c$, R$^d$, and R$^e$ is independently C$_1$–C$_{18}$ alkyl, cyclohexyl, phenyl, or C$_1$–C$_{18}$ alkoxy;
(h) each R$^f$ and R$^g$ is independently C$_1$–C$_{12}$ alkoxy, phenoxy, C$_1$–C$_{12}$ alkyl, C$_5$–C$_{12}$ cycloalkyl, benzyl, tolyl, or phenyl;
(i) each R$^1$, R$^2$ and R$^4$ is independently hydrogen, hydrocarbyl, functional hydrocarbyl, —O(hydrocarbyl), —O(functional hydrocarbyl), —SR, halogen, —SO$_3$R, —COOR, —COR, —OCOR, —NRR or cyano;
(j) each R$^3$ is independently R, —OR, —SR, halogen, —SO$_3$R, —COOR, —COR, —NRR or cyano; and
(k) n is an integer between 2 and about 50.

35. The composition of claim 34, wherein said composition is a coating composition.

36. The composition of claim 34, wherein the compound of formula (I), (II) or (III) is present in an amount from about 0.01 to about 20% by weight of the binder.

37. The composition of claim 36, wherein the compound of formula (I), (II) or (III) is present in an amount from about 0.1 to about 10% by weight of the binder.

38. The composition of claim 34, wherein said binder comprises a polymer.

39. The composition of claim 34, wherein the binder comprises an alkyd, acrylic, polyester, phenolic, melamine, epoxy or polyurethane resin, or blends thereof.

40. The composition of claim 34, wherein said binder is at least one of:
(a) cold- or hot-crosslinkable alkyd, acrylate, polyester, epoxy or melamine resins or mixtures of such resins;
(b) a two-component polyurethane system comprising hydroxyl-containing acrylate, polyester or polyether resins and aliphatic or aromatic isocyanates, isocyanurates or polyisocyanates;
(c) a one-component polyurethane system comprising blocked isocyanates, isocyanurates or polyisocyanates which are deblocked during baking;
(d) a two-component system comprising (poly)ketimines and aliphatic or aromatic isocyanates, isocyanurates or polyisocyanates;
(e) a two-component system comprising (poly)ketimines and an unsaturated acrylate resin or a polyacetoacetate resin or a methacrylamidoglycolate methyl ester;
(f) a two-component system comprising carboxyl- or amino-containing polyacrylates and polyepoxides;
(g) a two-component system comprising acrylate resins containing anhydride groups and on a polyhydroxy or polyamino component;
(h) a two-component system comprising (poly)oxazolines and acrylate resins containing anhydride groups, or unsaturated acrylate resins, or aliphatic or aromatic isocyanates, isocyanurates or polyisocyanates;
(i) a two-component system comprising unsaturated polyacrylates and polymalonates;
(j) a thermoplastic polyacrylate system comprising thermoplastic acrylate resins or externally crosslinking acrylate resins in combination with etherified melamine resins; and
(k) a system comprising siloxane-modified or fluorine-modified acrylate resins.

41. The composition of claim 40, which further comprises a curing catalyst.

42. The composition of claim 40, wherein said composition is a radiation-curable composition.

43. The composition of claim 40, wherein said composition further comprises an additional stabilizer against actinic radiation.

44. The composition of claim 43, wherein said additional stabilizer is present in an amount from about 0.05 to about 5% by weight of the binder.

45. The composition of claim 43, wherein said additional stabilizer is a sterically hindered amine or a UV absorber.

46. The composition of claim 45, wherein said sterically hindered amine comprises at least one member of the group consisting of: bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5dione; a mixture of 4-hexadecyloxy- and 4-stearyloxy-2,2,6,6-tetramethylpiperidine; the condensate of N,N'-bis(2,2,6,6-tetramethylpiperidin- 4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; N-(2,2,6,6-tetramethyl piperidin-4-yl)-n-dodecylsuccinimide; N-(1,2,2,6,6-pentamethylpiperidin-4-yl)-n-dodecylsuccinimide; 2-undecyl-7,7,9,9-tetramethyl-1-oxa-3,8-diaza-4-oxospiro[4.5]decane; the reaction product of 7,7,9,9-tetramethyl-2-cycloundecyl-1-oxa-3,8-diaza-4-oxospiro[4.5]decane and epichlorohydrin; derivatives thereof, and mixtures thereof.

47. The composition of claim 45, wherein said sterically hindered amine comprises at least one member of the group consisting of: bis(2,2,6,6-tetramethylpiperidin-4-yl) sebacate; bis(1,2,2,6,6-pentamethylpiperidin-4-yl)sebacate; bis(1-octyloxy-2,2,6,6-tetramethylpiperidin-4-yl)sebacate; the condensate of N,N'-bis(2,2,6,6-tetramethylpiperidin-4-yl) hexamethylenediamine and 4-tert-octylamino-2,6-dichloro-1,3,5-triazine; the condensate of N,N'-bis(2,2,6,6-tetramethylpiperidin-4-yl)hexamethylenediamine and 4-morpholino-2,6-dichloro-1,3,5-triazine; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl)pyrrolidin-2,5-dione; a mixture of 4-hexadecyloxy- and 4-stearyloxy-2,2,6,6-tetramethylpiperidine, and mixtures thereof.

48. The composition of claim 45, wherein said benzotriazole comprises at least one member of the group consisting of: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; [R—CH$_2$CH—COO(CH$_2$)$_3$]$_2$—where R=3'-tert-butyl-4'-hydroxy-5'-2H-benzotriazol-2-ylphenyl; and derivatives thereof.

49. The composition of claim 45, wherein said benzotriazole comprises at least one member of the group consisting of: 2-(2'-hydroxy-5'-(1,1,3,3-tetramethylbutyl)phenyl) benzotriazole; 2-(3',5'-di-tert-amyl-2'-hydroxphenyl) benzotriazole; 2-(3',5'-bis(α,α-dimethylbenzyl)-2'-hydroxyphenyl)benzotriazole; 2-(3'-tert-butyl-2'-hydroxy-5'-(2-octyloxycarbonylethyl)phenyl)benzotriazole, the transesterification product of 2-[3'-tert-butyl-5'-(2-methoxycarbonylethyl)-2'-hydroxyphenyl]benzotriazole with polyethylene glycol 300 and mixtures thereof.

50. The composition of claim 40, wherein said composition is a coating composition.

51. A photographic material comprising the light stabilizing composition of claim 40.

52. An actinic radiation stabilizing composition which comprises a polymer and at least one compound of formula (I), (II) or (III) according to claim 1.

53. The composition of claim 52, wherein said compound is chemically bound to said polymer.

* * * * *